(12) United States Patent
Lee

(10) Patent No.: US 11,103,310 B2
(45) Date of Patent: Aug. 31, 2021

(54) LASER IRRADIATION APPARATUS AND METHOD USING ROBOT ARM

(71) Applicant: OH & LEE MEDICAL ROBOT, INC., Daejeon (KR)

(72) Inventor: Jung Ho Lee, Daejeon (KR)

(73) Assignee: OH & LEE MEDICAL ROBOT, INC., Daejeon (KR)

( * ) Notice: Subject to any disclaimer, the term of this patent is extended or adjusted under 35 U.S.C. 154(b) by 69 days.

(21) Appl. No.: 16/094,821

(22) PCT Filed: Mar. 29, 2017

(86) PCT No.: PCT/KR2017/003440
§ 371 (c)(1),
(2) Date: Oct. 18, 2018

(87) PCT Pub. No.: WO2017/183825
PCT Pub. Date: Oct. 26, 2017

(65) Prior Publication Data
US 2019/0117307 A1    Apr. 25, 2019

(30) Foreign Application Priority Data

Apr. 19, 2016 (KR) .......................... 10-2016-0047353
Apr. 19, 2016 (KR) .......................... 10-2016-0047354

(51) Int. Cl.
*A61B 18/00* (2006.01)
*A61B 18/20* (2006.01)
(Continued)

(52) U.S. Cl.
CPC .......... *A61B 18/203* (2013.01); *A61B 5/0064* (2013.01); *A61B 18/201* (2013.01);
(Continued)

(58) Field of Classification Search
CPC ........ A61B 18/203; A61B 2018/00452; A61B 34/30
See application file for complete search history.

(56) References Cited

U.S. PATENT DOCUMENTS 4,697,590 A * 10/1987 Nakai .................. A61B 18/203
                                                        362/401
7,083,611 B2    8/2006 Lemchen
(Continued)

FOREIGN PATENT DOCUMENTS

CN      105169570 A    12/2015
KR      10-1015881 B1  2/2011
(Continued)

*Primary Examiner* — Michael J D Abreu
(74) *Attorney, Agent, or Firm* — Novick, Kim & Lee, PLLC; Sang Ho Lee; Hyun Woo Shin

(57) ABSTRACT

Provided are a laser irradiation apparatus using a robot arm and a method thereof which can automatically scan an object and irradiate with laser beam to the surface of the object based on the scanned information. The laser irradiation method using a robot, includes: collecting a raw data by scanning an object; constituting a three-dimensional image of the object on the basis of the raw data; setting a region of interest (ROI) on a surface of the object in the three-dimensional image; setting a guide path passing through the region of interest; and irradiating a laser on the surface of the object corresponding to the guide path using the robot arm having an end-effector.

8 Claims, 28 Drawing Sheets

(51) Int. Cl.
*A61N 5/06* (2006.01)
*A61B 34/30* (2016.01)
*A61B 5/00* (2006.01)
*A61N 5/067* (2006.01)
*A61B 90/00* (2016.01)
*A61B 18/18* (2006.01)

(52) U.S. Cl.
CPC ............ *A61B 34/30* (2016.02); *A61N 5/06* (2013.01); *A61N 5/0616* (2013.01); *A61B 5/441* (2013.01); *A61B 2018/00452* (2013.01); *A61B 2018/00904* (2013.01); *A61B 2018/1807* (2013.01); *A61B 2090/3612* (2016.02); *A61N 2005/067* (2013.01); *A61N 2005/0643* (2013.01)

(56) References Cited

U.S. PATENT DOCUMENTS

| | | |
|---|---|---|
| 2005/0137584 A1 | 6/2005 | Lemchen |
| 2007/0106306 A1* | 5/2007 | Bodduluri ............ A61B 34/32 606/133 |
| 2008/0033410 A1 | 2/2008 | Rastegar et al. |
| 2008/0151263 A1* | 6/2008 | Randers-Pehrson .... C40B 30/10 356/601 |
| 2008/0247637 A1 | 10/2008 | Gildenberg |
| 2010/0094265 A1 | 4/2010 | Rastegar et al. |
| 2010/0141729 A1* | 6/2010 | Petsch ................... B41M 5/267 347/225 |
| 2012/0071794 A1 | 3/2012 | Karni |
| 2015/0057675 A1 | 2/2015 | Akeel et al. |
| 2016/0016312 A1 | 1/2016 | Lawrence et al. |

FOREIGN PATENT DOCUMENTS

| | | |
|---|---|---|
| KR | 10-2015-0135536 A | 12/2015 |
| WO | 2011/159118 A2 | 6/2011 |
| WO | 2015/051661 A1 | 4/2014 |

\* cited by examiner

LASER IRRADIATION APPARATUS AND METHOD USING ROBOT ARM

TECHNICAL FIELD

The present invention relates to a laser irradiation apparatus using a robot arm and a method thereof.

BACKGROUND ART

Today, a variety of laser treatment methods by irradiating the laser beam on the skin have been developed to achieve the purpose of treatment, etc., and have been still actively studying a medical laser apparatus for use the laser treatment methods.

The treatment methods using the laser has been using for a variety of purposes such as to promote hair growth or prevent hair loss, skin peel, skin regeneration, skin whitening, wrinkle or spot removal, or stain removal, etc.

However, a user, such as a physician, manually operates the laser treatment apparatus to perform the treatment in the conventional art.

Accordingly, there is a problem in that the reliability of the treatment may be decreased by lowering the accuracy of the treatment.

In addition, conventionally, there is an additional problem that of the treatment time for taking the laser is excessively too long.

DISCLOSURE

Technical Problem

An object of the present invention is to provide a laser irradiation apparatus using a robot arm and a method thereof, which can automatically scan an object and irradiate with the laser beam on the surface of the object based on the scanned information.

Technical Solution

The laser irradiation method using a robot arm in accordance with one embodiment of the present invention, includes collecting a raw data by scanning an object; constituting a three-dimensional image of the object on the basis of the raw data; setting a region of interest (ROI) on a surface of the object in the three-dimensional image; setting a guide path passing through the region of interest; and irradiating a laser on the surface of the object corresponding to the guide path using the robot arm having an end-effector.

On the other hand, the laser irradiation method is making a computer program for performing him may be provided in the program itself or stored in a recording medium, it can be performed by the laser irradiation apparatus according to an embodiment of the present invention.

The laser irradiation apparatus using a robot arm in accordance with an embodiment of the present invention includes a scanner for scanning an object to collect a raw data; a vision controlling unit for constituting a three-dimensional image of the object on the basis of the raw data, and setting a region of interest (ROI) on the surface of the object in the three-dimensional image; a motion controlling unit for setting a guide path passing through the region of interest; and a robot arm, having an end-effector, for irradiating a laser on the surface of the object corresponding to the guide path.

In addition, the laser irradiation apparatus may use a wired or wireless network such as the Internet may be controlled as described above in conjunction with an external server.

In addition, the robot arm comprises a first base part; a second base part being coupled to be rotatable on the first base part; a first link being coupled to be rotatable on the second base part; a second link being coupled to be rotatable on the first link; an auxiliary link having one end coupled to the second base part and the other end coupled to the second link; a laser unit, arranged on the first base part, for generating the laser, a first motor pal, arranged on the first base pal, for rotating the second base part; a second motor part, arranged on the second base part, for rotating the first link; and a third motor part, arranged on the second base part, for rotating the second link through the auxiliary link.

Advantageous Effects

A laser irradiation apparatus using a robot arm and a method thereof according to the present invention have effects that of improving the accuracy of the laser treatment and effectively reducing the operational time required for the laser treatment.

DESCRIPTION OF DRAWINGS

The accompanying drawings, which are included to provide a further understanding of the invention and are incorporated in and constitute a part of this specification, illustrate embodiments of the invention and together with the description serve to explain the principles of the invention.

BEST MODE

Figure 1:
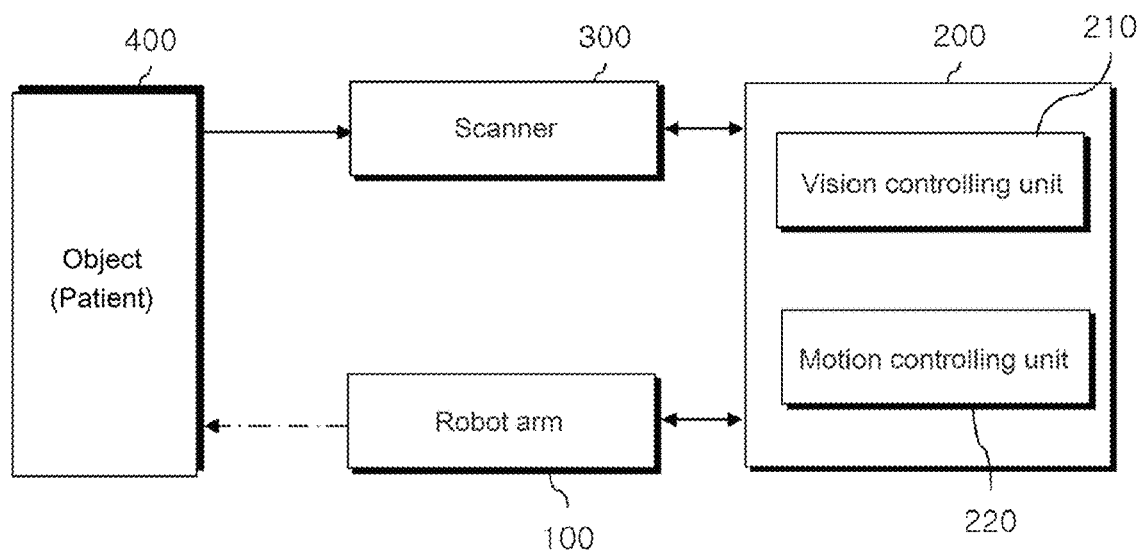
FIGS. 1 to 3 are block diagrams for explaining embodiments for the overall structure of a laser irradiation apparatus according to the present invention.

Detailed exemplary embodiments of the present invention will be described with reference to the accompanying drawings.

The present invention may be modified in various ways and implemented by various exemplary embodiments, so that specific exemplary embodiments are illustrated in the drawings and will be described in detail below. However, it is to be understood that the present invention is not limited to the specific exemplary embodiments, but includes all modifications, equivalents, and substitutions included in the spirit and the scope of the present invention.

On the other hand, although the first and/or the terms of the second and so on in the present invention can be used in describing various elements, but the above elements shall not be restricted to the above terms. These terms are only to distinguish one component from other components, for example within that range departing from the scope of the concept of the present invention, a first element could be termed a second element. Similarly, the second component may be named as a first component.

As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, it will be understood that when an element is referred to as being "directly connected" or "directly coupled" to another element, there are no intervening elements present.

The terminology used herein is for the purpose of describing particular embodiments only and is not intended to be limiting of the invention. As used herein, the singular forms are intended to include the plural forms as well, unless the context clearly indicates otherwise.

It will be further understood that the terms "comprises." "comprising." "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The accompanying drawings are intended to illustrate aspects of the present invention, but the scope of the present invention is not limited to this. In addition, the attached drawings will be noted that the portion or component is disposed is enlarged/reduced to better explain the characteristics of the present invention.

In the following description, it is explained as an example that the laser is irradiated to the facial skin of a patient for ease of explanation, but an apparatus and a method according to the present invention may be applied whatever as long as irradiating the laser on the surface of a given object.

Hereinafter, a laser irradiation apparatus using a robot arm and a method thereof according to the present invention is described in detail with reference to the accompanying drawings.

Figure 2:
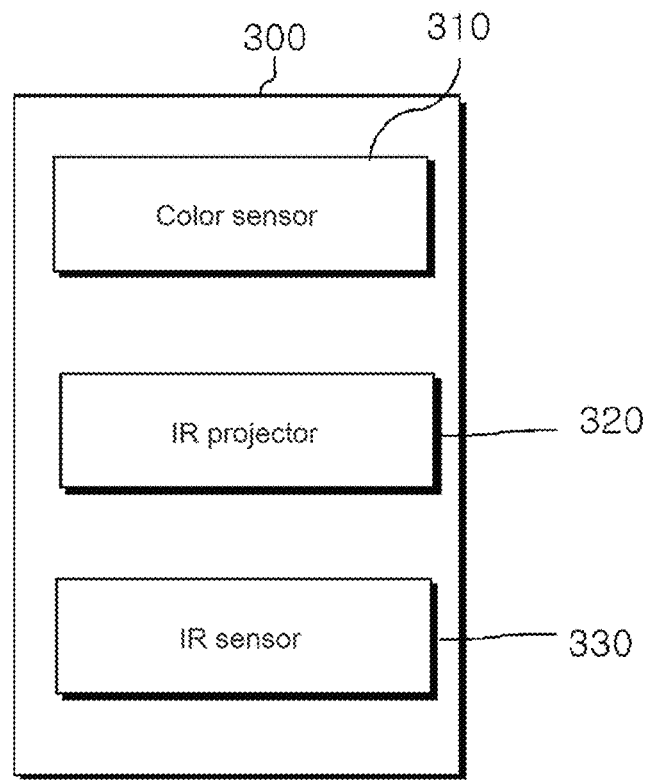
Figure 3:
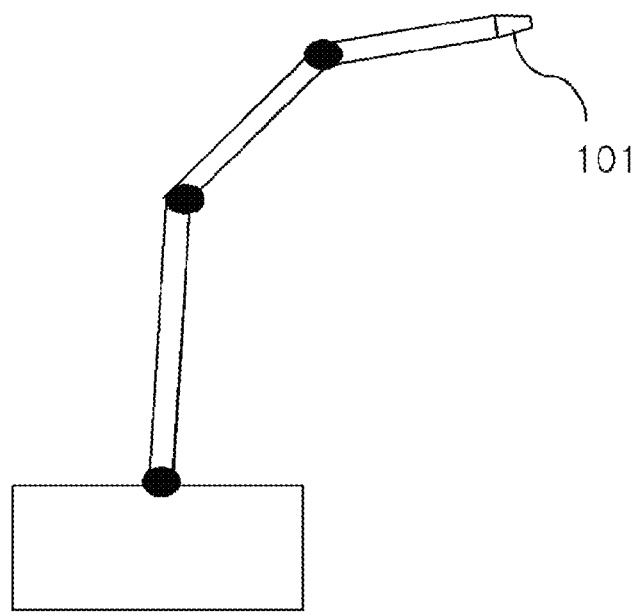

FIGS. 1 to 3 are block diagrams for explaining embodiments for the overall structure of the laser irradiation apparatus according to the present invention.

Referring to FIG. 1, the laser irradiation apparatus 10 may include a scanner 300, a robot arm 100, and a controlling unit 200.

The scanner 300 may collect raw data by scanning an object. Here, the raw data may include two-dimensional image and depth information.

The two-dimensional image may include color information, the diagnosis of the particular condition, such as telangiectasia may be possible according to the color information of a patient's skin. Further, the scanner may detect the size, location, or depth information, etc. for pores, scars, or wrinkles of the patient's face using the two-dimensional images and the depth information.

The scanner 300, as shown in FIG. 2, may include a color sensor 310 for photographing the two-dimensional color images, and an IR projector 320 and an IR sensor 330 for obtaining the three-dimensional depth data.

If the IR projector 320 may irradiate the IR light on the surface of an object 400, that is the surface of the patients' skin, the IR sensor 330 would obtain the depth data by detecting the IR light reflected from the surface of the object 400.

The color sensor 310 may obtain the two-dimensional color image by photographing the surface of the object.

The robot arm 100 may have an end-effector (EE) 101, as shown in FIG. 3, and irradiates the laser on the surface of the object 400 according to the control of the controlling unit 200. Specifically, the robot arm 100 may irradiate with the laser to the surface of the object 400 in response to a guide path (GP) through the end-effector 101. Such the robot arm 100 may be considered as a manipulator.

The controlling unit 200 may control the overall function and operation of the laser irradiation apparatus 10.

The controlling unit 200 may include a vision controlling unit 210 and a motion controlling unit 220.

The vision controlling unit 210 may receive the raw data having the two-dimensional image and the depth information transmitted from the scanner 300, and configure the three-dimensional image of the object 400 on the basis of the raw data.

Here, the origin position of the raw data and the direction of the coordinates may vary depending on the object 400, for example, the shape and volume of the face, or various causes such as the scan starting point of the scanner 300, etc.

In addition, the vision controlling unit 210 may adjust the coordinates in alignment for the raw data. For this adjustment, the vision controlling unit 210 may detect the position of objects such as eyes, or a nose using face recognition algorithm, and obtain aligning homogeneous matrix.

The vision controlling unit 210 may set a region of interest (ROI) on the surface of the object 400 in the three-dimensional image.

The region of interest (ROI) may be a region including a portion that of requiring the laser irradiation, and set the region of interest (ROI) may be set by the user (e.g., physician), or may be automatically set by the three-dimensional image process.

For example, the user may set the region of interest (ROI) by clicking on the four corner points on the facial surface, and in this case, the normal vector corresponding to each of the corner point may be obtained.

On the other hand, the vision controlling unit 210 may determine at least one of the color or the contrast of the surface of the object 400 based on the data transmitted form the scanner 300, and set the region of interest based on the determined result.

Specifically, the vision controlling unit 210 may detect a portion where the color or/and the contrast of the surface of the object 400 is (or are) different form the two-dimensional color image of the object 400 photographed by the scanner 300. In addition, the vision controlling unit may set the region of the interest to be included the other portion where the color and/or contrast is (or are) different than another portion.

More specifically, the reason for darkly appearing a specific portion is mainly due to the pigment of the depth of the blood vessels, otherwise due to the shaded region by the contour of the skin.

Therefore, an algorithm may be applied to distinguish the regions which darkly appear due to the pigment or blood vessels of the face or darkly appear in the shade region due to the contour of the skin, and the dermatological treatment method may be changed depending on this distinction.

For example, if the shaded region, caused by the contour of the skin, is occurred, it is caused by the skin stain or the atrophy of the subcutaneous fat layer due to skin aging, thereby treating firmness treatment, fac implants, fillers, and the like.

Further, when the shaded region caused by the scar is occurred, it may be necessary the scar treatment.

In the following, it may be referred to as a region of therapy (ROT) which is necessary for treatment by irradiating the laser on the surface of the object.

For example, the region of therapy (ROT) may be liver spots, freckles, burn marks, tattoos, acne, dark circles, and the like, those are occurred in the human skin, the present invention is not limited to this, and it may be treatable regions by irradiating the laser of various kinds of wavelength or frequency.

The vision controlling unit 210 may determine this portion where color and/or contrast are different surroundings as the region of therapy (ROT).

According to an embodiment of the present invention, the region of interest (ROI) and the region of therapy (ROT) may be set separately as described above, but may be set only the region of therapy (ROT) which is actually irradiated as needed.

The vision controlling unit 210 constitutes a motion pattern on the object for the laser treatment on the basis of the determined (or set) information as described above, and the motion pattern may be configured by setting the guide path (GP) passing through the region of interest (ROI) or the region of therapy (ROT).

Then, the vision controlling unit 210 sets a plurality of points arranged on the guide path (GP). The plurality of points may represent the position where the laser is irradiated on the surface of the object, and the point on the guide path (GP) displayed on the two-dimensional image may be projected on the three-dimensional image.

In addition, the vision controlling unit 210 obtains the actual laser irradiation points to be irradiated on the surface of the object by selecting only those points positioned within the region of therapy (ROT) of the plurality of points arranged on the guide path (GP).

The motion controlling unit 220 controls the operation of the robot arm 100 on the basis of the information obtained by the vision controlling unit 210, while the end-effector 101 irradiates the laser as closely moving to the surface of the object.

Here, the interval between the surface of both the end-effector 101 and the surface of the object during the laser irradiation are preferably and constantly maintained during the movement, the interval may be set based on a focal distance of the laser.

For example, the motion controlling unit 220 may control the movement and the laser irradiation of the robot arm 100 on the basis of the guide path (GP) and the laser irradiation points set in the vision controlling unit 210.

In addition, the motion controlling unit 220 may emergently stop the laser irradiation by urgently stopping the robot arm 100, for example, the operation of the robot arm 100 may be stopped by the action or the voice of the doctor or the patient.

The laser irradiation apparatus 10 according to the present invention may each operate in a manual mode or an automatic mode.

For example, in the automatic mode, the scanner 300 scans the surface of the object 400 to obtain the information about the surface of the object 400, and the controlling unit 200 may irradiate with the laser on the surface of the object 400 by controlling the robotic arm 100 on basis of the obtained information.

On the other hand, in the manual mode, the user such as a doctor has the controlling authorization, the robot arm 100 is operated by the control of the user.

It has been described for the configuration of the laser irradiation apparatus with FIGS. 1 to 3 as described above, the present invention shall not be limited, and some of the illustrated elements may be omitted or added additional elements as needed.

For example, the laser irradiation apparatus 10 further includes a computing unit (not shown) for performing a function of Artificial Intelligence (AI) and a database (not shown) for processing big data.

The laser irradiation method using the laser irradiation apparatus 10 according to the present invention will be described in detail with reference to the accompanying drawings.

FIGS. 4 to 25 are views for explaining the operation of the laser irradiation apparatus according to embodiments of the present invention, the same explanation as explained with reference to FIGS. 1-3 of the operation and the construction of the laser irradiation apparatus 10 will be omitted below.

Figure 4:
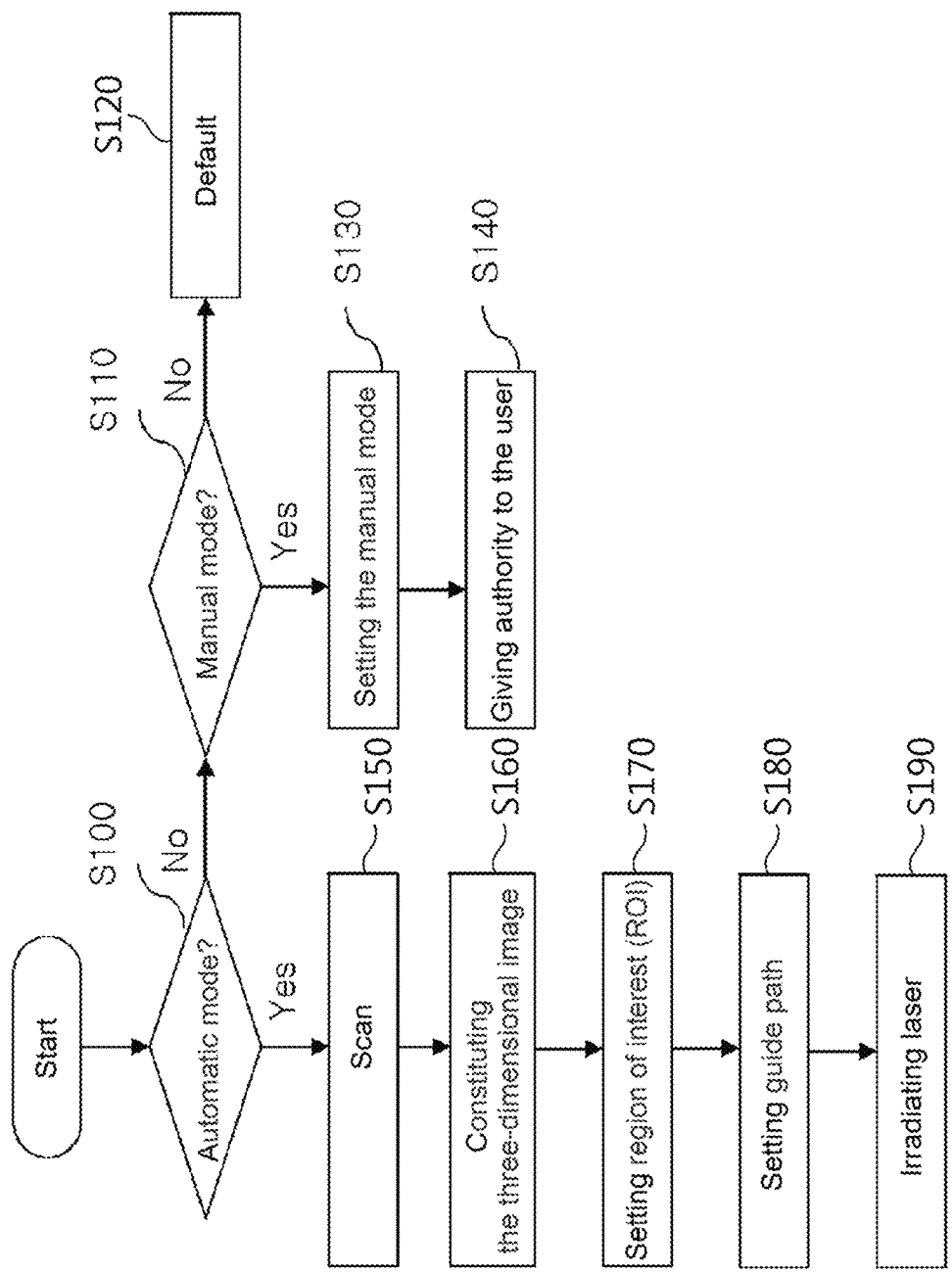
FIGS. 4 to 25 are views for explaining the operation of a laser irradiation apparatus according to the present invention.
Figure 5:
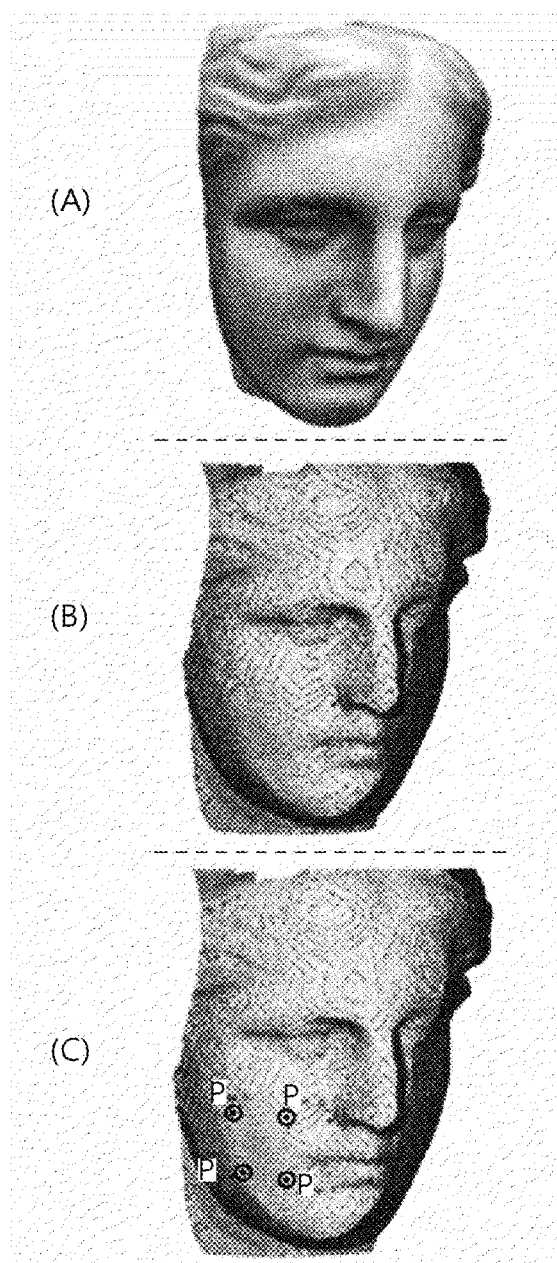

Referring to FIG. 4, the controlling unit determines whether the current setting mode is the automatic mode or not or not (step S100). If the automatic mode is not, the controlling unit determines whether the current setting mode is the manual mode or not (S110).

For example, the user may set by selecting one of the manual mode or the automatic mode using a button mounted in the laser irradiation apparatus 10 or a user interface (UI) provided in a touch screen.

It is determined that if the current setting mode is not the manual mode in the step S110, it is performed a different function previously predetermined (for example. Default setting) (S120).

On the other hand, if the current setting mode is the manual mode, it is determined that the setting status of the manual mode (S130), the controlling authorization is given to the user (S140).

Here, the operation of giving the controlling authorization to the user means that the controlling unit 200 may judge for themselves and limit the operation of the robot arm 100.

In the manual mode, the user may operate the robotic arm 100 on their own while performing the laser treatment.

On the other hand, it is determined that the current setting mode is the automatic mode in the step S100, the scanner 300 scans the surface of the object 400 according to the control of the controller 200 (S150). As a result of the scanning by the scanner 300, the raw data including the two-dimensional image and the depth information may be generated.

Here, a screen mode is available to be moved the irradiation position of the laser along the motion of the pointer on a monitor.

Then, the vision controlling unit 210 constitutes the three-dimensional image on the basis of the raw data obtained from the scanner 300 (S160).

For example, the canner may scan a plaster cast of a head shape of a person, as shown FIG. 5(A), it may be constituted the three-dimensional image as shown FIG. 5(B).

Hereinafter, for convenience of explanation, it will be described where the plaster cast of the head shape is regarded as the object 400.

After constituting the three-dimensional image, the region of interest (ROI) is set on the surface of the object 400 in the three-dimensional image (S170).

For example, the first corner point (Pcor, 1), the second corner point (Pcor, two), the third corner point (Pcor, 3), and the four corner point (Pcor, 4) may be set on the surface of the object 400 in the three-dimensional image, as shown in FIG. 5(C). Then, the region of interest (ROI) may be set with a region partitioned by the vertices with four corner points such as the first, the second, the third and the four corner points.

In this embodiment, the region of interest (ROI) is set using the four corner points, but the number of corner points to be used the conditions may be changed. For example, it is possible to set the region of interest (ROI) by using at least three corner points.

Hereinafter, the first corner point (Pcor, 1), the second corner point (Pcor, two), the third corner point (Pcor, 3), and the fourth corner point (Pcor, 4) may be referred as the first point (P1), the second point (P2), the third point (P3), and the fourth point (P4), respectively.

Then, the guide path (GP) passing through the region of interest (ROI) may be set (step S180).

Figure 6:
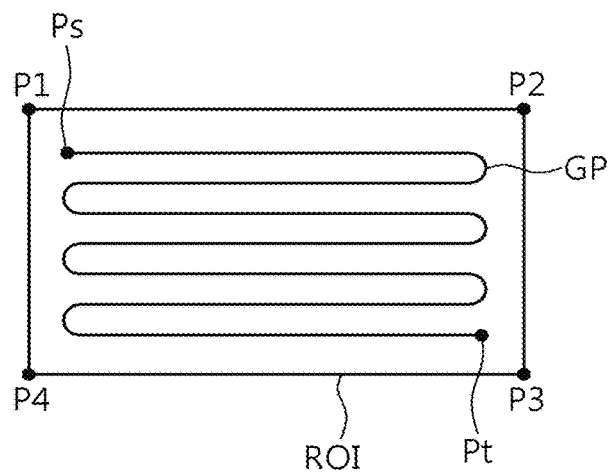

For example, as illustrated in FIG. 6, it is possible to set the guide path (GP) within the region of interest (ROI).

The starting point of the guide path (GP), i.e. the point at which the laser irradiation is started, is expressed as Ps, while the end point of the guide path (GP), i.e. the point at which the laser irradiation is ended, is expressed as Pt.

Then, the laser is irradiated in sequence to the laser irradiation points on the surface of the object corresponding to the guide path (GP) (Step S190).

The guide path (GP) may include a path where the robot arm 100 is irradiated with the laser. In other words, the robot arm 100 may irradiate with the laser to the surface of the object as moving in response to the guide path (GP).

The guide path (GP) may be regarded as including a path connecting the hitting point of the laser.

On the other hand, the regions of interest (ROI) may be set based on at least one a color, contrast, contour and texture of the surface of the object 400. It will be explained with reference to FIG. 7 as follows.

Figure 7:
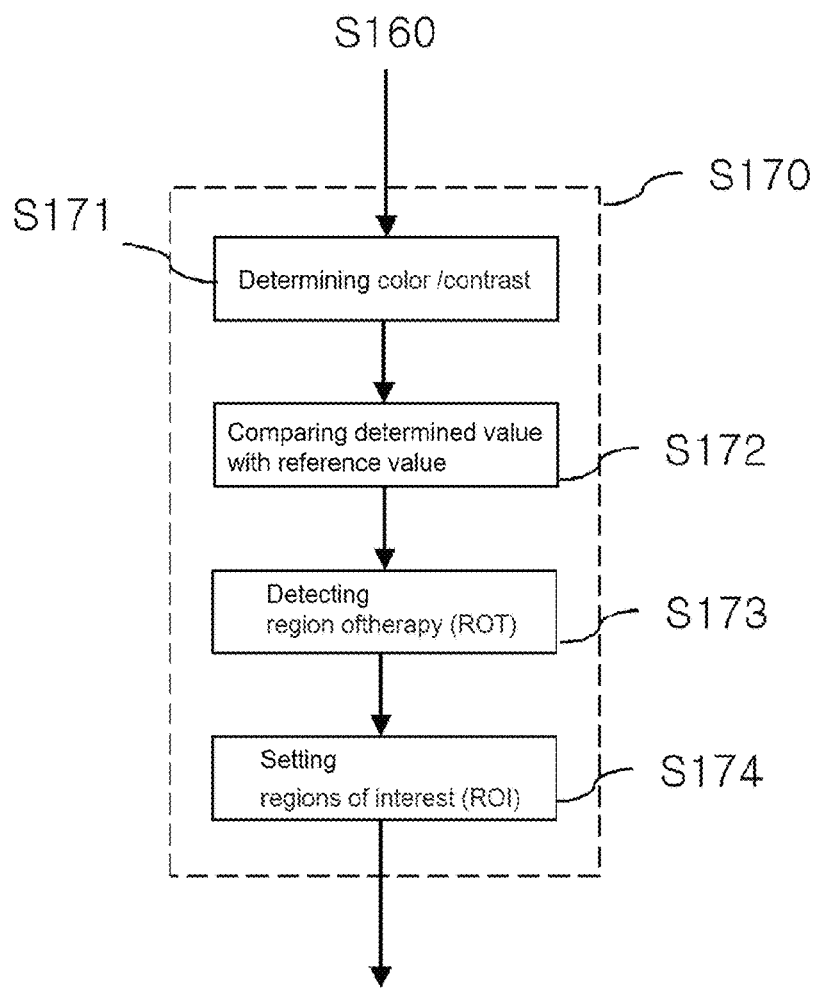

Referring to FIG. 7, in S170 step of setting the region of interest (ROI), the color and/or contrast of the surface of the object 400 is firstly determined (step S171). Here, the color and/or contrast of the surface of the object 400 may be determined from the two-dimensional color image of the object 400.

Since, the determined value is compared with the reference value (S172 step), the region of therapy (ROT), which is different surroundings at least one of contrast and contour, is detected from the surface of the object 400 according to the comparison result (step S173).

For example, a region of normal (RON) and the region of therapy (ROT) may be distinguished on the basis of at least one of a color, contrast, contour and texture on the surface of the object 400.

Figure 8:
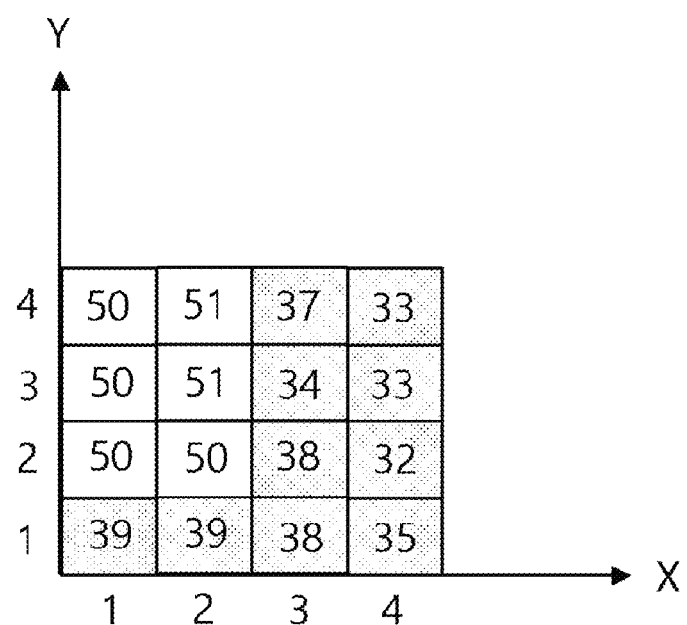

As shown in FIG. 8, when the total 16 of unit areas are arranged in 4×4 matrix form, the number expressed on each of the unit area may indicate the brightness value.

Here, it is assumed that the brightness value is 40, it is determined the region of therapy (ROT) with unit areas of (1, 1), (2, 1), (3, 1), (3, 2), (3, 3), (3, 4), (4, 1), (4, 2), (4, 3) and (4, 4) that the brightness value is smaller than 40, and the remained portion may be determined as the region of normal (RON).

The brightness of the region of therapy (ROT) may appear relatively darker than other portion, that is lower than the brightness of the region of normal (RON). Similarly, the color of the region of therapy (ROT) may appear relatively thicker than the color of the region of normal (RON). The thicker color means more darker than surroundings.

As such, the brightness value of the region of therapy (ROT) may be a lower portion than a predetermined reference brightness value. The reference brightness value may be varied in various ways depending on the surface state or characteristics (for example, contour or texture, etc.) of the object 400 or other factors such as the color tone.

Here, the reference brightness value may be a constant, but preferably may be set differently for each patient or treatment region. For example, the reference brightness value may be varied by considering a brightness value of the surrounding region to coincide the skin tone with a region adjacent to the region of therapy (ROT).

If the face of White is bright as a whole, the reference brightness value may be set relatively high based on the brightness value. The reason is that if the face is appeared with bright white as a whole, a portion requiring the treatment such as dots, spots required. i.e. the region of therapy, is more prominently appeared.

On the other hand, if the face is Mongoloid appeared relatively dark as a whole than Whites, the reference brightness value may be set relatively low compared with the brightness value of Whites.

After detecting the region of therapy (ROT), then the regions of interest (ROI) is set (S174).

As described above, the region of interest (ROI) includes the region of therapy (ROT), the region of interest (ROI) and the region of therapy (ROT) may be equally set.

As illustrated in FIG. 9(A), it is assumed that the region of therapy (ROT), where brightness, color, contour, and texture, etc. are different within the region of normal RON, is included on a predetermined region (R 1) of the surface of the object 400, the form of the region of therapy (ROT) is arbitrarily set for convenience of the description and the present invention is not limited thereto.

In this case, as illustrated in FIG. 9(B), it may be set the first, second, third, and fourth points (P1, P2, P3, and P4) to be contacted the first line (L1) connecting the first point (P1) and the second point (P2) with the region of therapy (ROT), the second line (L2) connecting the second point (P2) and the fourth point (P4) with the region of therapy (ROT), the third line (L3) connecting the third point (P3) and the fourth point (P4) with the region of therapy (ROT), and the fourth line (L4) connecting the fourth point (P4) and the first point (P1) with the region of therapy (ROT).

In addition, regions divided with the first, the second, the third, and the fourth points (P1, P2, P3, and P4) may be set as the region of interest (ROI).

Here, the region of therapy (ROT) may be also included inside of the region of normal (RON), the region of interest (ROI) may include one portion of the region of normal (RON) as well as the region of therapy (ROT).

Hereinafter, it is assumed that a portion included within the region of interest (ROI) in the region of normal (RON) is a second region of normal (RON2) and the other portion does not include within the region of interest (ROI) in the region of normal (RON) is a first region of normal (RON1).

Figure 9:
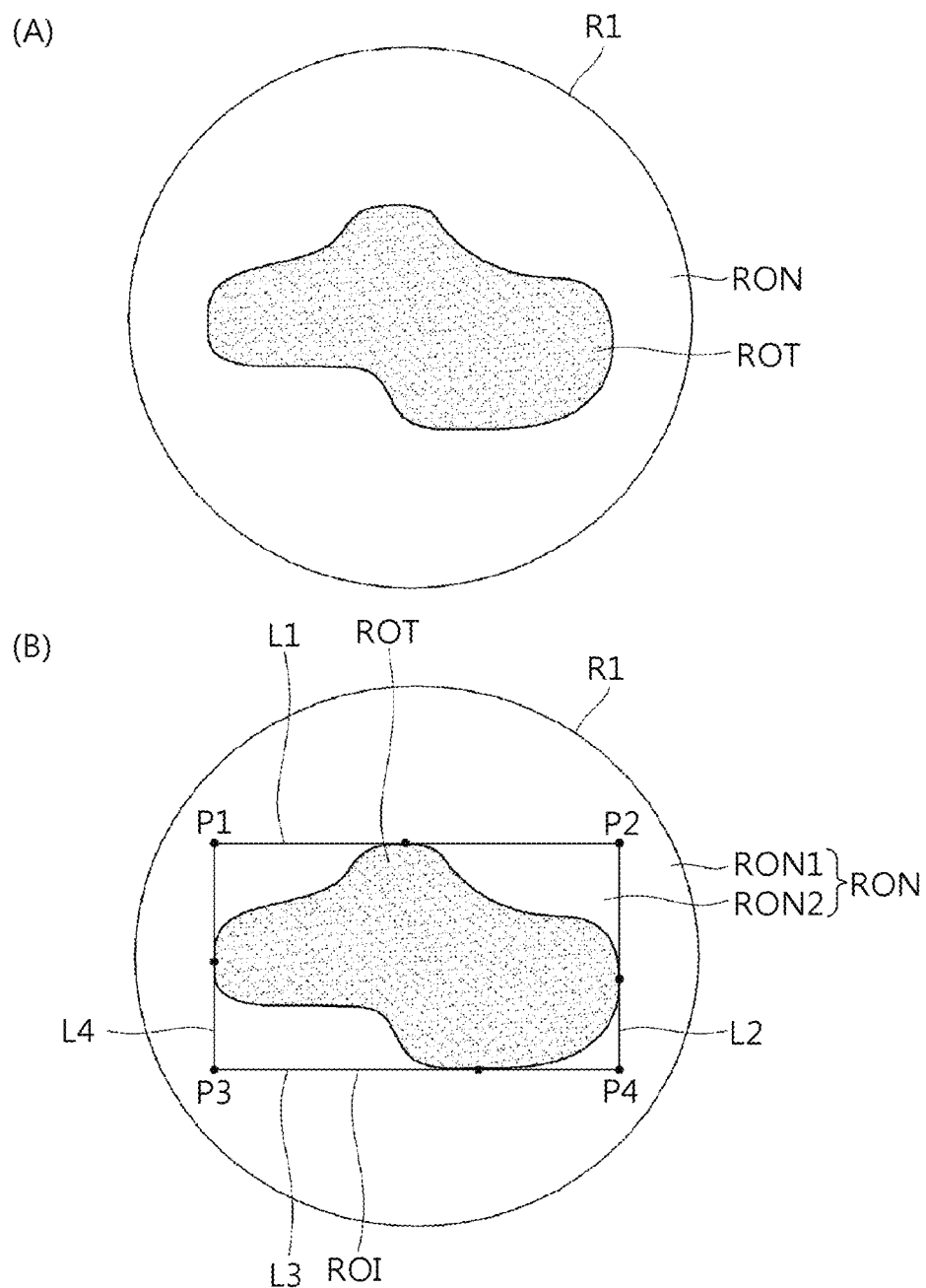

In the case of FIG. 9, as setting the region of interest (ROI), it is described only one case that a line connecting two near points is contacted on the region of therapy (ROT), the present invention may not be limited thereto.

Figure 10:
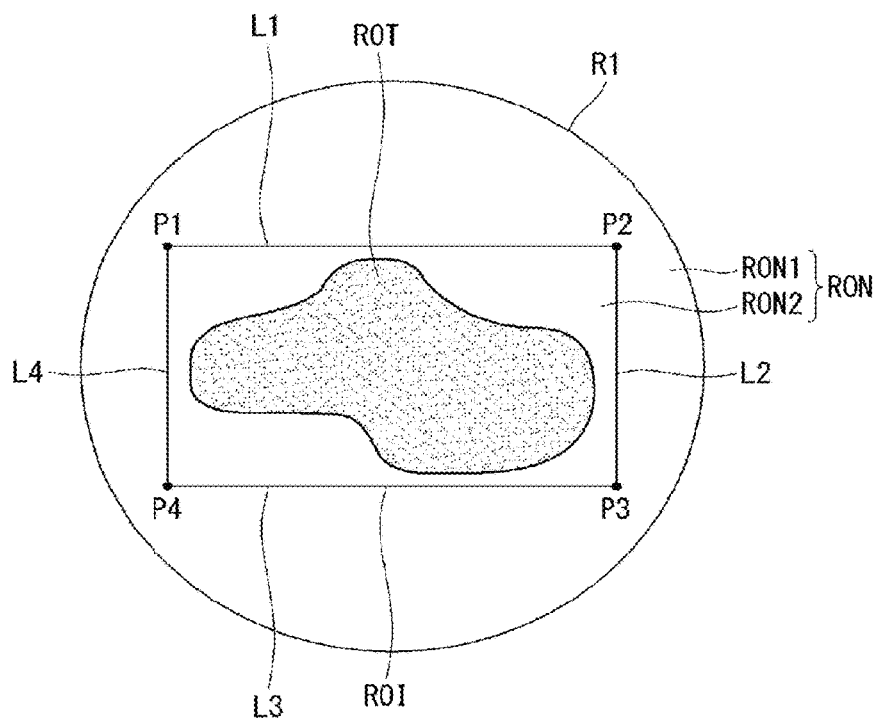

For example, as in a case of FIG. 10, at least one or all lines (L1, L2, L3, and L4) connecting two near points is (or are) not in contact with the region of therapy (ROT).

Thus, the method of setting the region of interest (ROI) may be changed in various ways.

In case that the shape of the region of therapy (ROT) is the polygonal shape, it may be occurred that the region of therapy (ROT) and the region of interest (ROI) are same depending on the set position of the point.

On the other hand, the guide path (GP) is capable of being set within the region of therapy (ROT).

Figure 11:
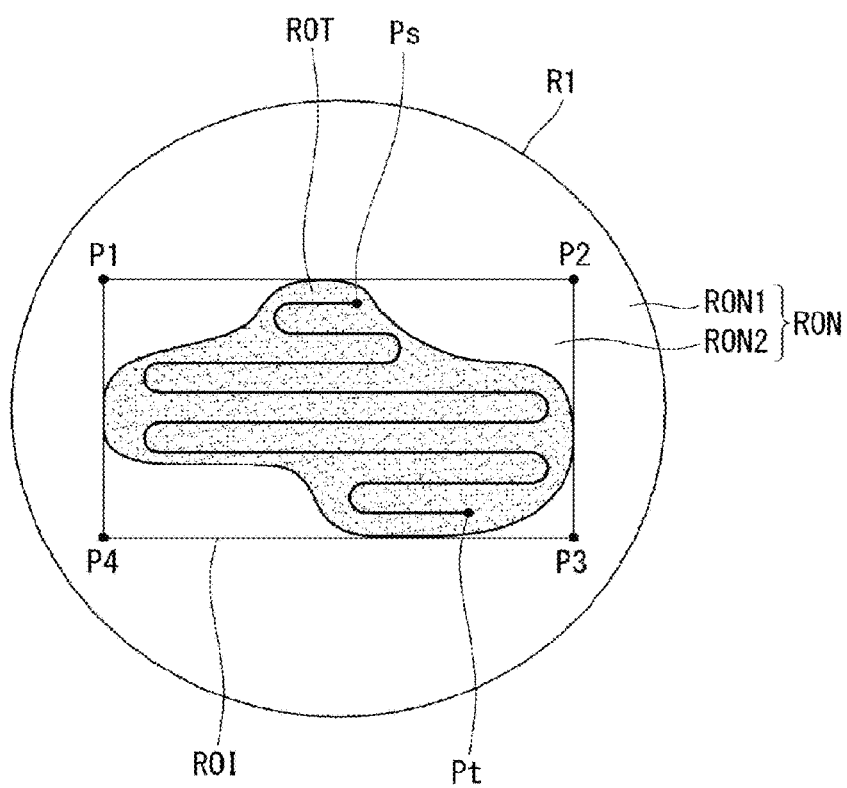
Figure 12:
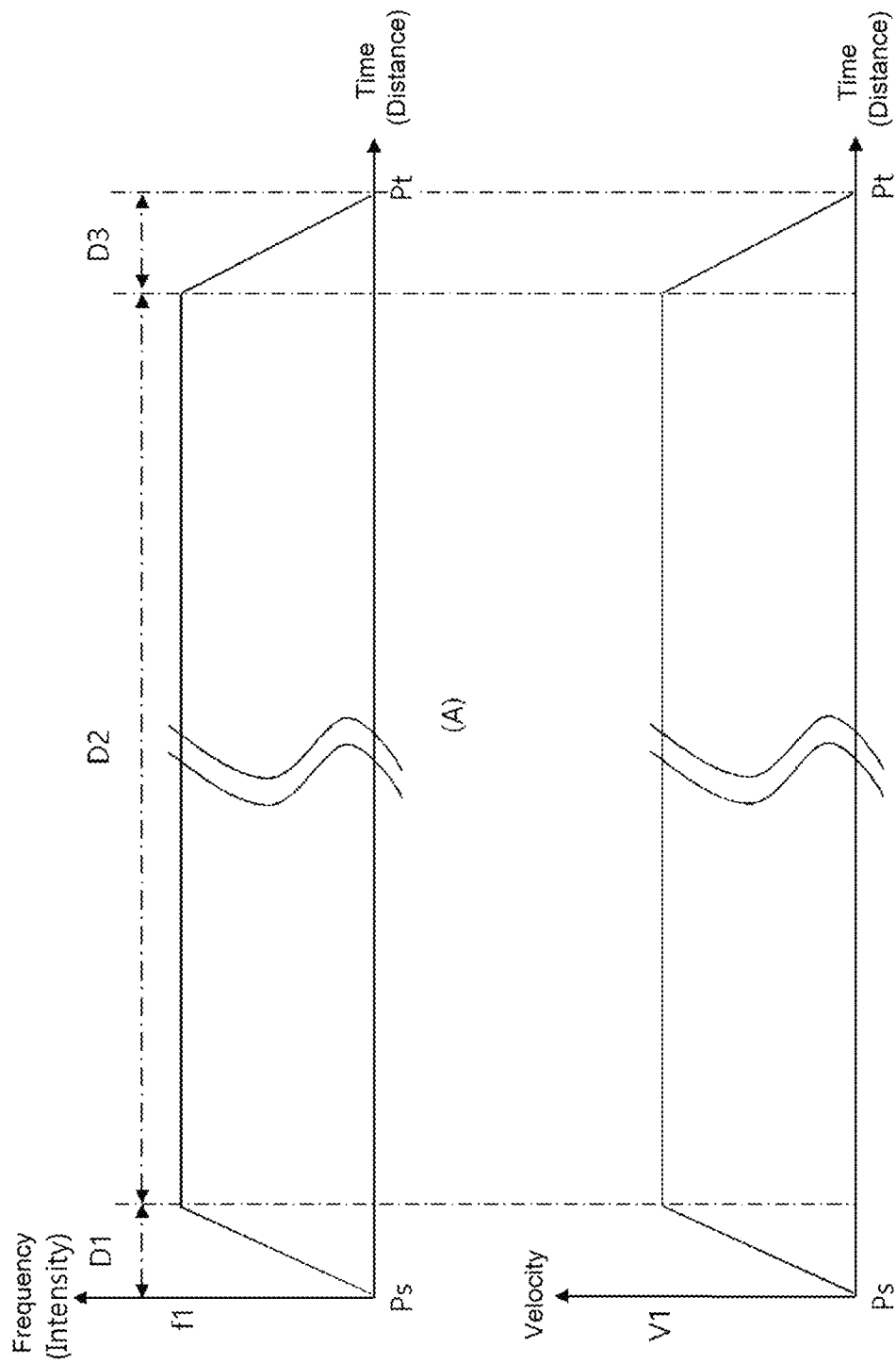
Figure 13:
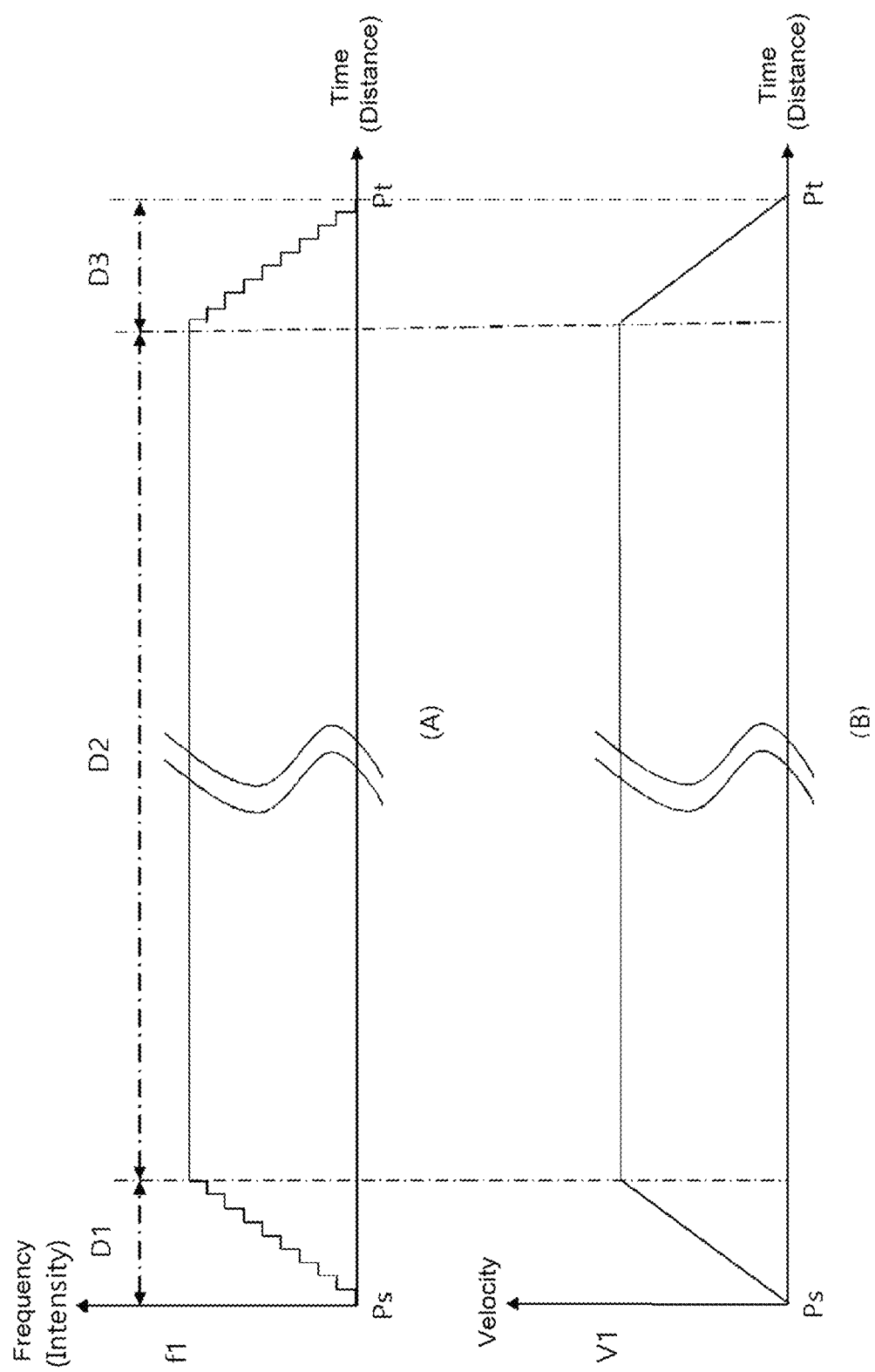

For example, it is possible to set the guide path (GP) with the zigzag form within the region of therapy (ROT), as shown in FIG. 11.

As such, the guide path (GP) is passing through the region of therapy (ROT), the laser is capable of being irradiated in the region of therapy (ROT).

On the other hand, it is possible to control the fluence and/or frequency of the laser in the beginning step and the end step of the laser irradiation.

The fluence of the laser represents the laser energy ($J/cm^2$) delivered per unit area, it may means the strength or intensity of the laser. And the laser frequency may means the emission frequency of the laser.

Referring to FIG. 12(A), at least one of the fluence or frequency of the laser is gradually raised in the beginning step of irradiating the laser, while at least one of the fluence or frequency of the laser is gradually decreased in the end step of the irradiating the laser.

In the following description, the beginning step of the laser irradiation is referred to an acceleration section (D1), while the end step of the laser irradiation is referred to a reduction section (D3).

As shown in FIG. 12(B), the moving speed of the robot arm 100 may be increased in the acceleration section (D1). That is, the movement speed of the robot arm 100 may be accelerated.

The occurrence reason of the acceleration section (D1) is because it takes some time from the time of supplying the power operating the robot arm 100 to the motor to the time of reaching the desired rotation speed.

In addition, in the deceleration section (D3), the moving speed of the robot arm 100 may be reduced. The reason why the deceleration section D3 is generated is that it takes some time from the time of shutting out the power supply to the motor operating the robot arm 100 to the stop of the motor similarly to the acceleration section D1.

In this way, when the fluence and/or frequency of the laser is gradually risen in acceleration section (D1) and is gradually decreased in the deceleration section (D3), it may be possible to uniformly irradiate the laser.

The fluence and/or frequency of the laser may be substantially proportional to the moving speed of the robot arm 100.

At this time, a maintain section (D2) may be occurred between the acceleration section (D1) and the deceleration section (D3), the fluence and/or frequency may substantially and constantly be maintained in the maintain section (D2) if the laser irradiation is not stopped.

The speed of the robot arm 100 may be substantially and constantly maintained in the maintain section (D2), for example, the speed of the arm 100 may be constantly maintained during the section (D2) from the time at which the acceleration of the robot arm 100 is ended to the time at which the deceleration is started.

As shown in FIG. 13(A), it may be possible that of increasing with step curve the fluence and/or frequency of the laser in the acceleration section (D1) or decreasing in the deceleration section (D3).

In this case, it may be considered to gradually raise the fluence and/or frequency of the laser in the acceleration section (D), and gradually decrease the fluence and/or frequency of the laser in the deceleration section (D3).

On the other hand, the guide path (GP) may be possible to deviate outside the region of therapy (ROT) within the region of interest (ROI).

Figure 14:
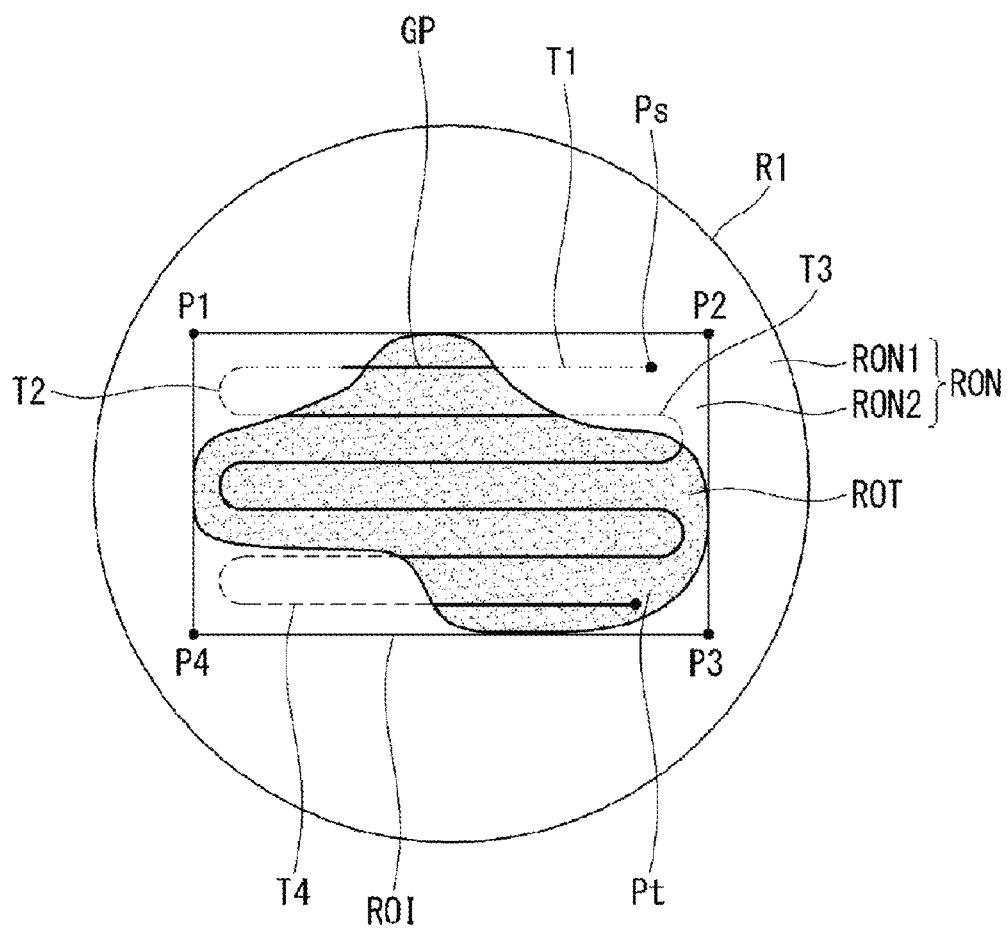

For example, as shown in FIG. 14 when the region of interest (ROI) include the region of therapy (ROT) and the region of normal, i.e., the second region of normal (RON2), the guide path (GP) may be passed all regions of the region of therapy (ROT) and the second region of normal (RON2).

In this case, the robot arm for irradiating the laser is turned on in correspondence to the region of therapy (ROT) or turned off in correspondence with the second region of normal (RON2).

Thus, it is possible to set the guide path (GP) without the relationship of the shape of the region of therapy (ROT) within the region of interest (ROI).

Further, the guide path (GP) includes a portion passing through the region of therapy (ROT) and the other portions (T1, T2, T3, and T4) passing through the region of normal (RON2) deviating outside the region of therapy (ROT).

Figure 15:
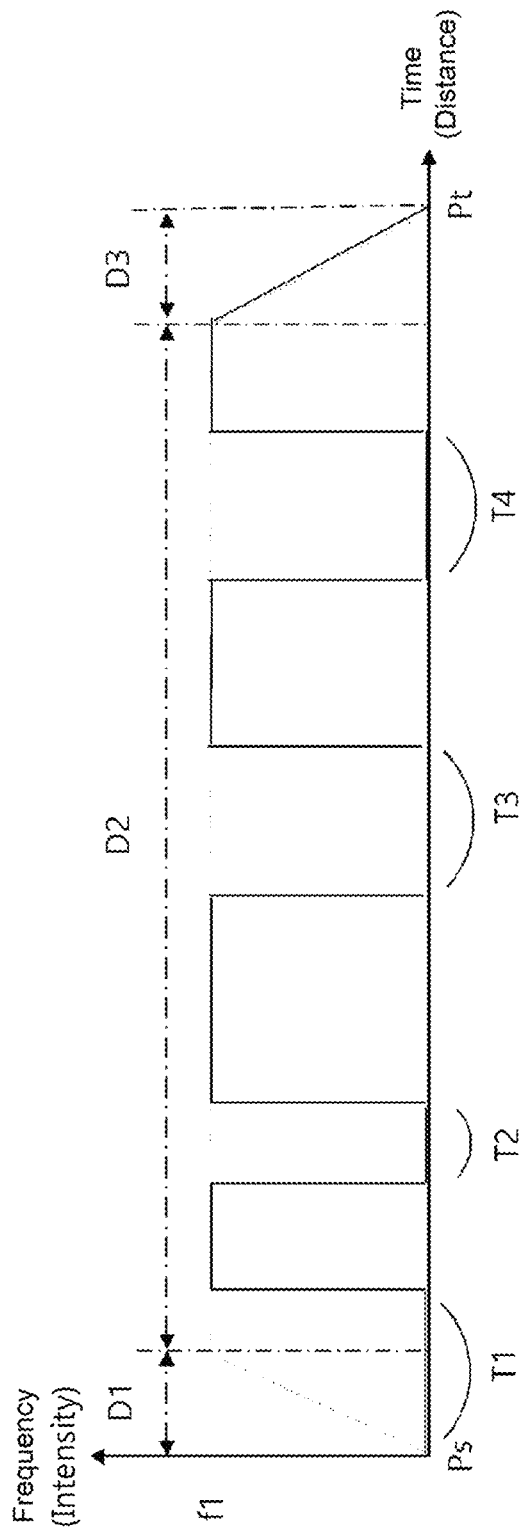

As shown in FIG. 15, the robot arm 100 may turn off the laser irradiation corresponding to the portion passing through the second region of normal (RON2) in the guide path (GP). In other words, it is considered that the robot arm 100 may turn on/off the laser irradiation depending on at least one color, brightness, and contour of the surface of the object 400 in the course of irradiating the laser along the guide path (GP).

That is, the robot arm 100 moves corresponding to the guide path (GP) and may turn on the laser irradiation corresponding to the portion, where the color is appeared more darker or the brightness is lower than the surroundings, that is the region of therapy (ROT) and turn off the laser irradiation corresponding to the portion, where the color is appeared more lighter or the brightness is higher than the surroundings, that is the region of normal (RON).

Referring to FIG. 15, it may be known that the laser frequency and/or fluence is set substantially zero in the portions (T1, T2, T3, and T4) where the robot arm 100 is passing through the second region of normal (RON2).

In this case, the movement of the robot arm is possible to maintain substantially and constantly, thereby improving the accuracy of the treatment.

On the other hand, it is possible to adjust at least one of the frequency, the irradiation time, the number of the laser irradiation, the fluence of the laser depending on the degree of color and/or brightness of the region of therapy (ROT) under the control of the motion controlling unit 220.

Figure 16:
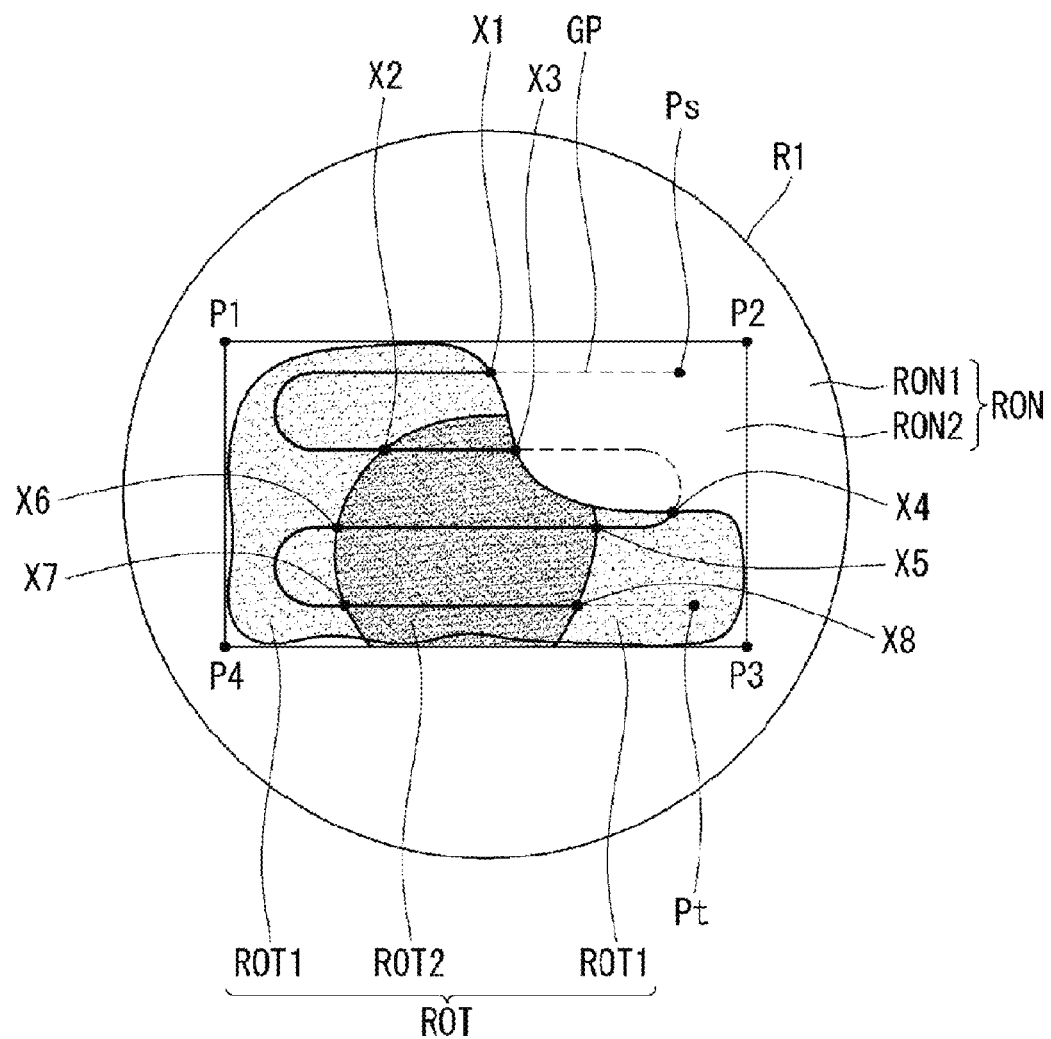

Referring to FIG. 16, the region of therapy (ROT) may include the first region of therapy (ROT1) and the second region of therapy (ROT2).

Here, the color of the second region of therapy (ROT2) may be darker than the first region of therapy (ROT1), or the brightness of the second region of therapy (ROT2) may be lower than the brightness of the first region of therapy (ROT1).

Alternatively, the brightness of the second region of therapy (ROT2) may be lower than the critical brightness value predetermined in advance, while the brightness of the first region of therapy (ROT1) may be higher than the critical brightness value predetermined in advance.

In this case, the second region of therapy (ROT2) may be considered as a portion required intensive care compared to the first region of therapy (ROT1).

In this embodiment of the present invention, it is referred to as the first point X1 for a boundary point between the second region of normal (RON2) and the first region of therapy (ROT1) on the guide path (GP) as sequentially moving at the starting point Ps of the laser, the second point X2 for a boundary point between the first region of therapy (ROT1) and the second region of therapy (ROT2), the third point X3 for a boundary point between the second region of therapy (RON2) and the second region of normal (ROT2), the fourth point X4 for a boundary point between the second region of normal (RON2) and the first region of therapy (ROT1), the fifth point X5 for a boundary point between the first region of therapy (ROT1) and the second region of therapy (ROT2), the sixth point X6 for a boundary point between the second region of therapy (ROT2) and the first region of therapy (ROT1), the seventh point X7 for a boundary point between the first region of therapy (ROT1) and the second region of therapy (ROT2), and the eighth point X8 for a boundary point between the second region of therapy (ROT2) and the first region of therapy (ROT).

Figure 17:
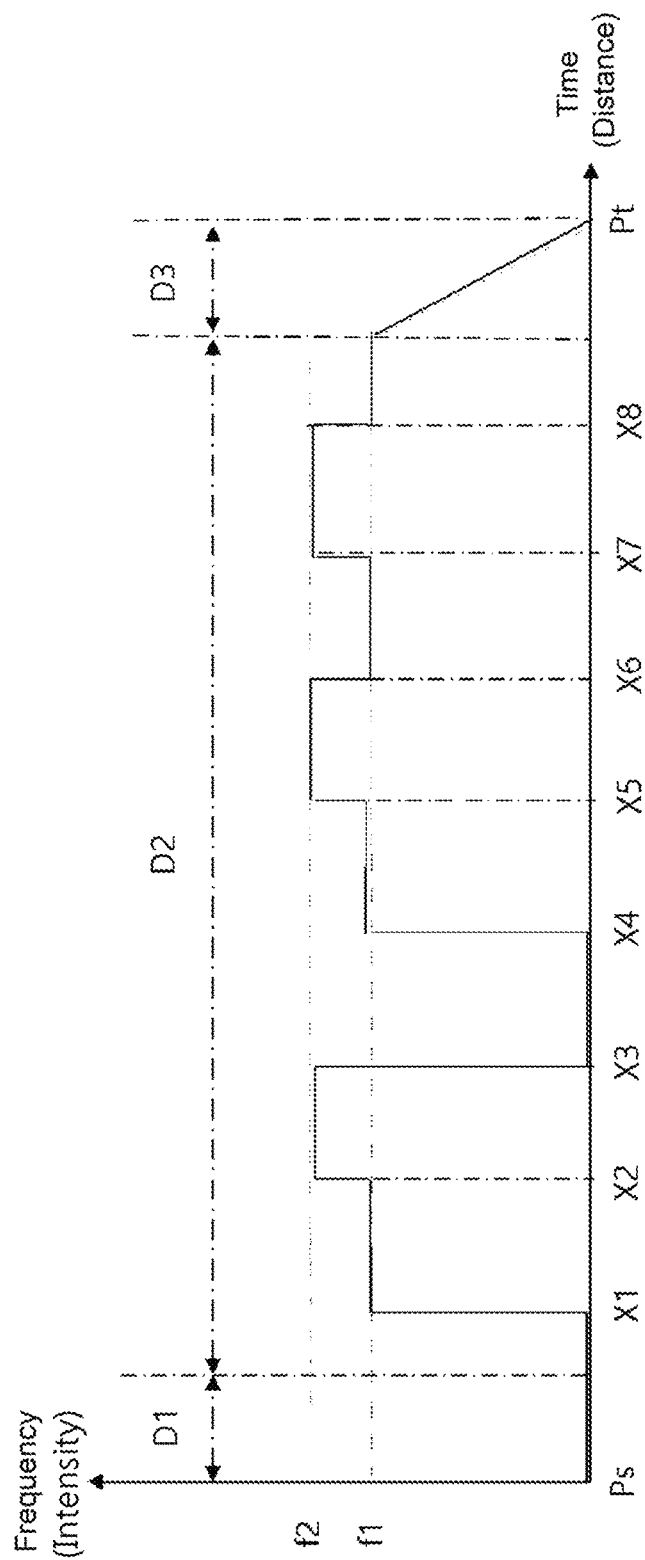
Figure 18:
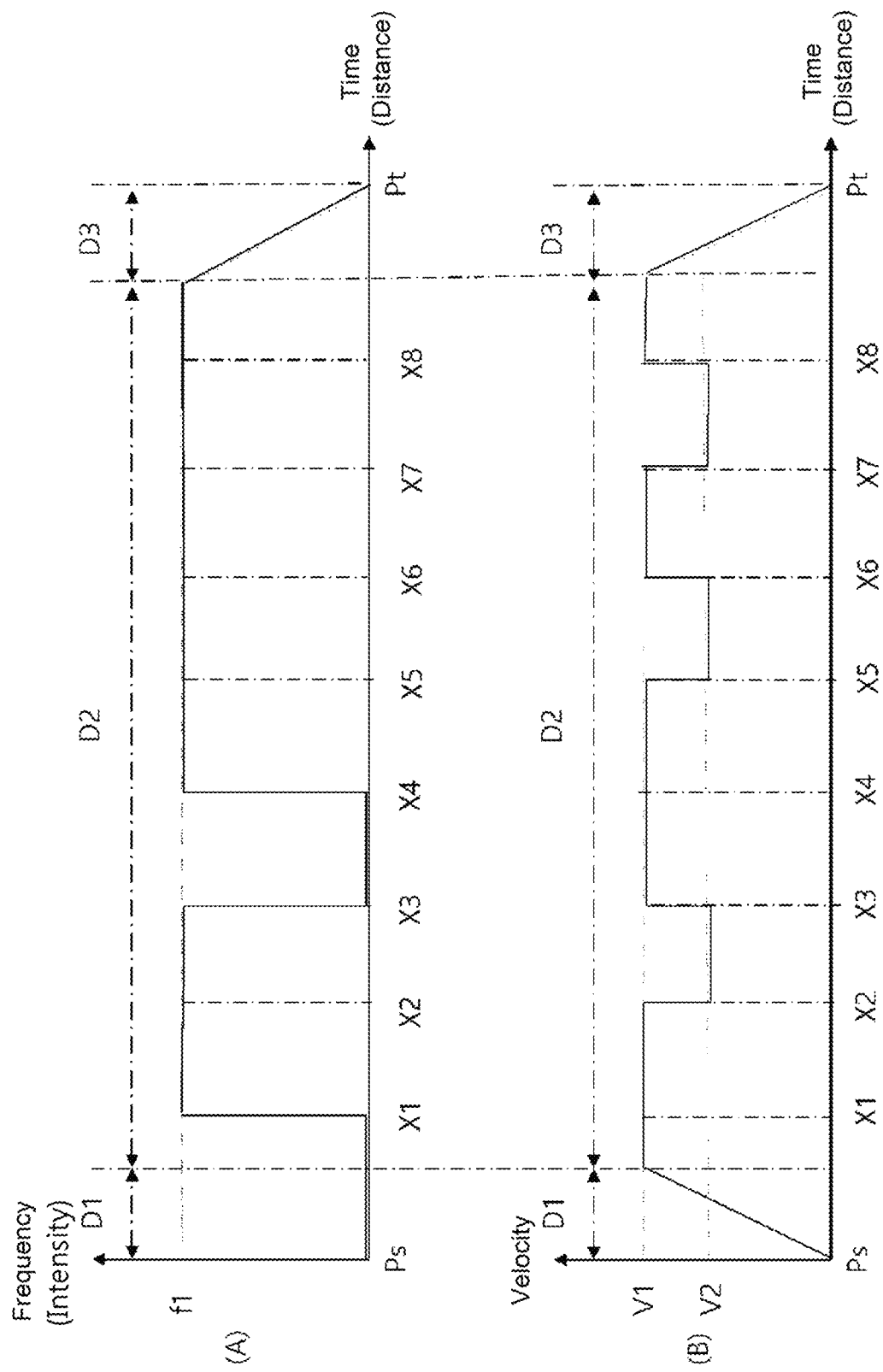
Figure 19:
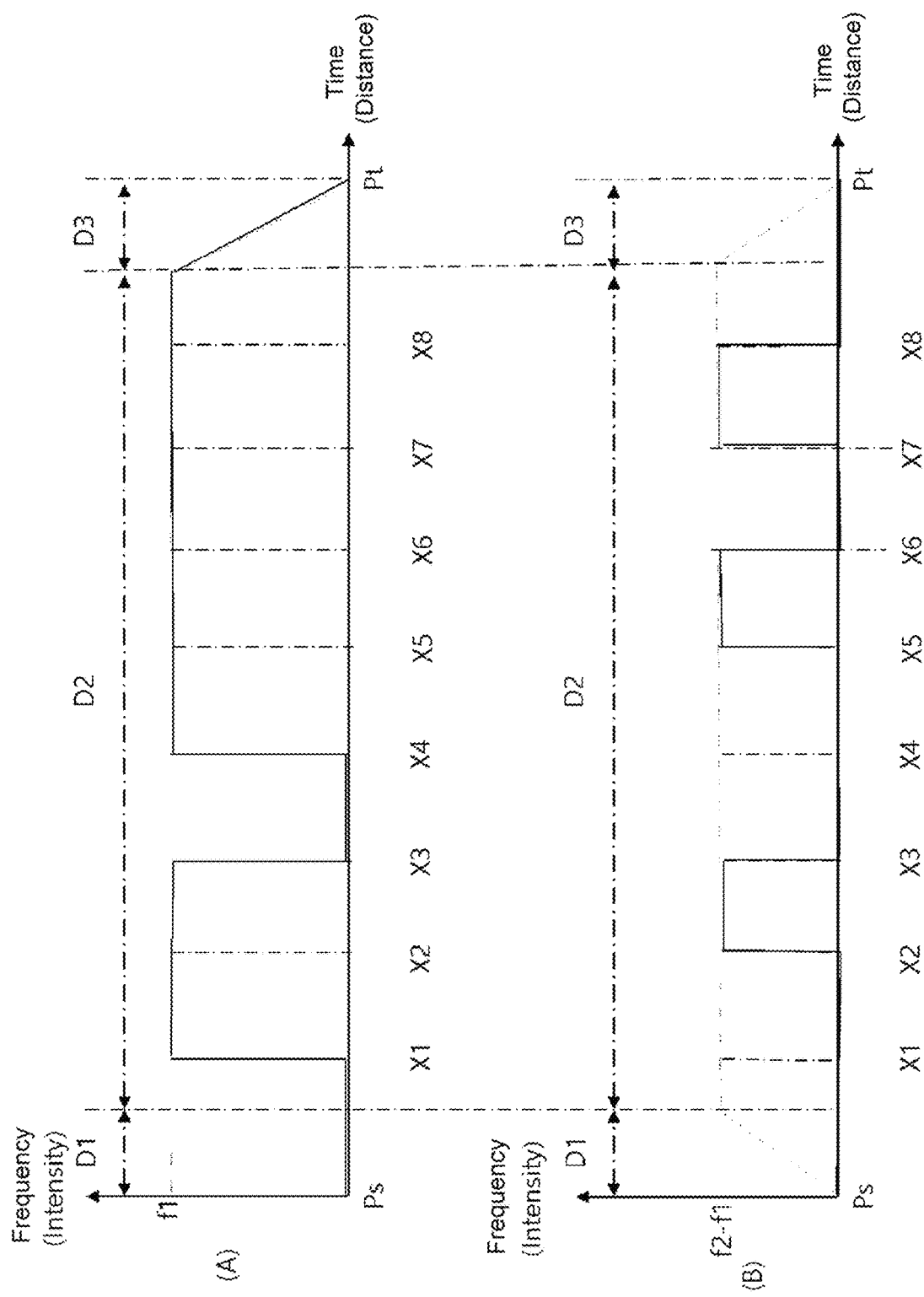

As shown in FIG. 17, the robot arm may turn off the laser irradiation in sections from the start point (Ps) of the laser to the first point (X1) and from the third point (X3) to the fourth point (X4), respectively.

For example, since Ps-X1 section and X3-X4 section are included in the second region of normal (RON2), thus the robot arm 100 may not irradiate the laser.

On the other hand, the frequency of the laser is set at the first frequency (f1) in X1-X2 section, X4-X5 section, X6-X7 section and the section from the eighth point (X8) to the beginning of the deceleration section (D3).

And, it may be gradually varied the gradation of the irradiation conditions through the variations of the laser irradiation frequency or the laser irradiation fluence by the variation in velocity of the end-effector 101, or the adjustment of the laser fluence or pulse duration in X1, X3 and X4 points.

Further, in the other points except X1, X3 and X4 points, the gradation of the irradiation conditions as described above may be gradually achieved.

On the other hand, in X2-X3, X5-X6, and X7-X8 sections, the frequency of the laser may set with a second frequency (f2) that is higher than the first frequency (f1).

In this case, the laser, which is relatively stronger, may be irradiated on the second region of therapy (ROT2) thereby improving the treatment efficiency.

Referring to FIG. 18(A), the frequency of the laser may equally set as the first frequency (f1) in X1-X3 section. X4-X8 section and a section from the eighth point (X8) to the beginning of the deceleration section (D3).

Thus, while maintaining the frequency of the laser, as shown in FIG. 18(B), the movement speed of the robot arm 100 may set at the first speed (V1) in a section from a point of the end of the acceleration section D1 to the second point X2, X3-X5 section, X6-X7 section, and the section from the eighth point (X8) to the beginning of the deceleration section (D3).

On the other hand, the movement speed of the robot arm 100 may be set at the second speed (V2) which is slower than the first speed (V1) in X2-X3, X5-X6, and X7-X8 sections.

In this case, the laser may irradiate relatively longer than the second region of therapy (ROT2) thereby improving the treatment efficiency.

That is, in the case that the speed of the end-effector (EE) and the fluence of the laser are constant and the emission frequency of the laser is higher, the overlapping rate of the laser is relatively higher in the second region of therapy (ROT2), thereby providing more amount of the laser energy.

On the other hand, for the second region of therapy (ROT2), the number of treatments may be set a lot more than the first region of therapy (ROT1). For this, it will be described below referring to FIG. 19.

FIG. 19(A) shows the status that the robot arm 100 may irradiate the laser for the first laser treatment on the surface of the object 400 along the guide path (GP) within the region of interest (ROI), while FIG. 19(B) shows the status that of performing the second laser irradiation carried out after the end of the first laser treatment.

Referring to FIG. 19(A), the robot arm 100 may irradiate the laser in X1-X3 section, X4-X8 section and a section from the eighth point (X8) to before the deceleration section (D3), in which the frequency of the laser may be equally set at the first frequency (f1).

Referring to FIG. 19(B), in the second course of the laser treatment, the robotic arm 100 may irradiate the laser in X2-X3 section, X5-X6 section, and X7-X8 section corresponding to the second region of therapy (ROT2), in which it may be equally set to the frequency of the laser corresponding to the difference between the second frequency (f2) and the first frequency (f1).

Thus, the therapeutic effect similar to that of irradiating the laser of the second frequency (f2) may be occurred in the second region of therapy (ROT2).

Figure 20:
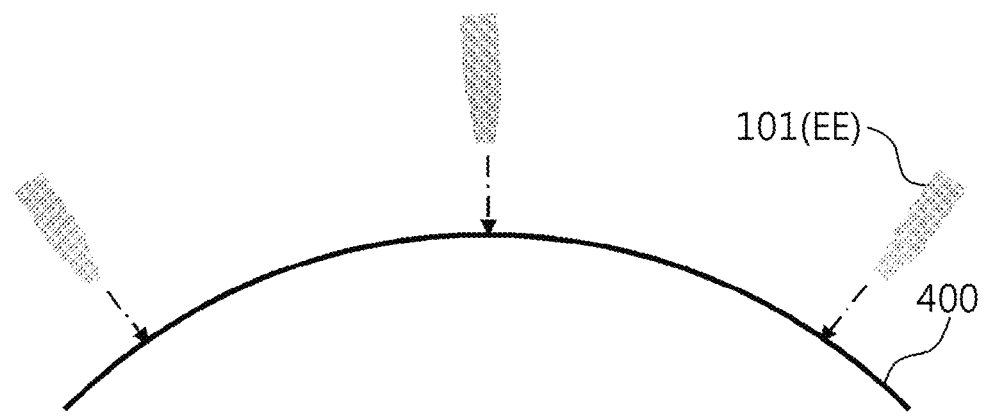

According to the present invention, as in the case of FIG. 20, the end-effector 101 of the robot arm 100 preferably irradiates the laser approximately perpendicular to the surface of the object 400 to increase the therapeutic efficacy and to improve the treatment accuracy.

To this end, the robot arm 100 may be desirable with degree of freedom (DOF). Specifically, the robot arm 100 may be desirable to have five degrees of freedom, and it is preferably have at least six degrees of freedom for exceptional circumstances.

Figure 21:
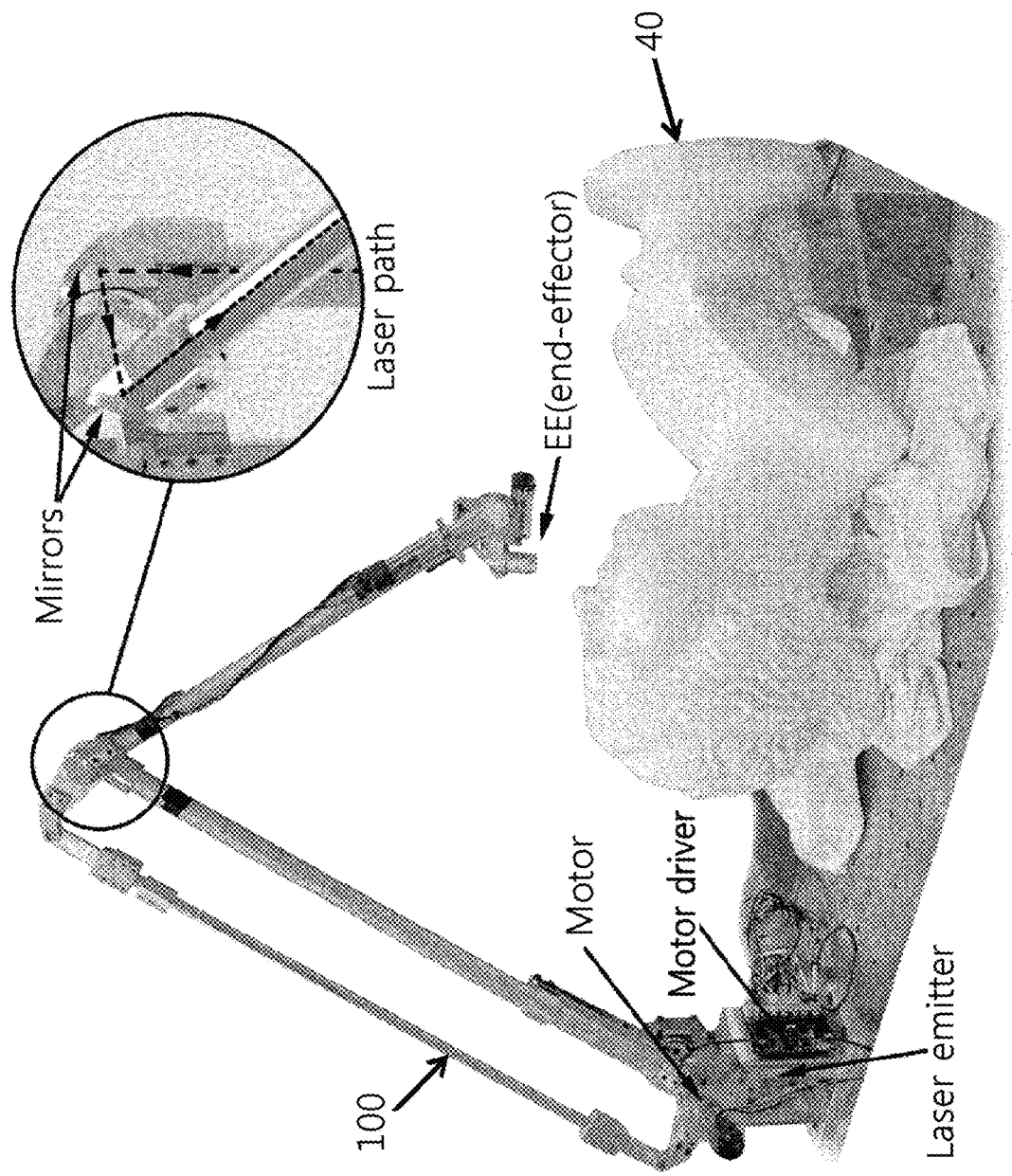
Figure 22:
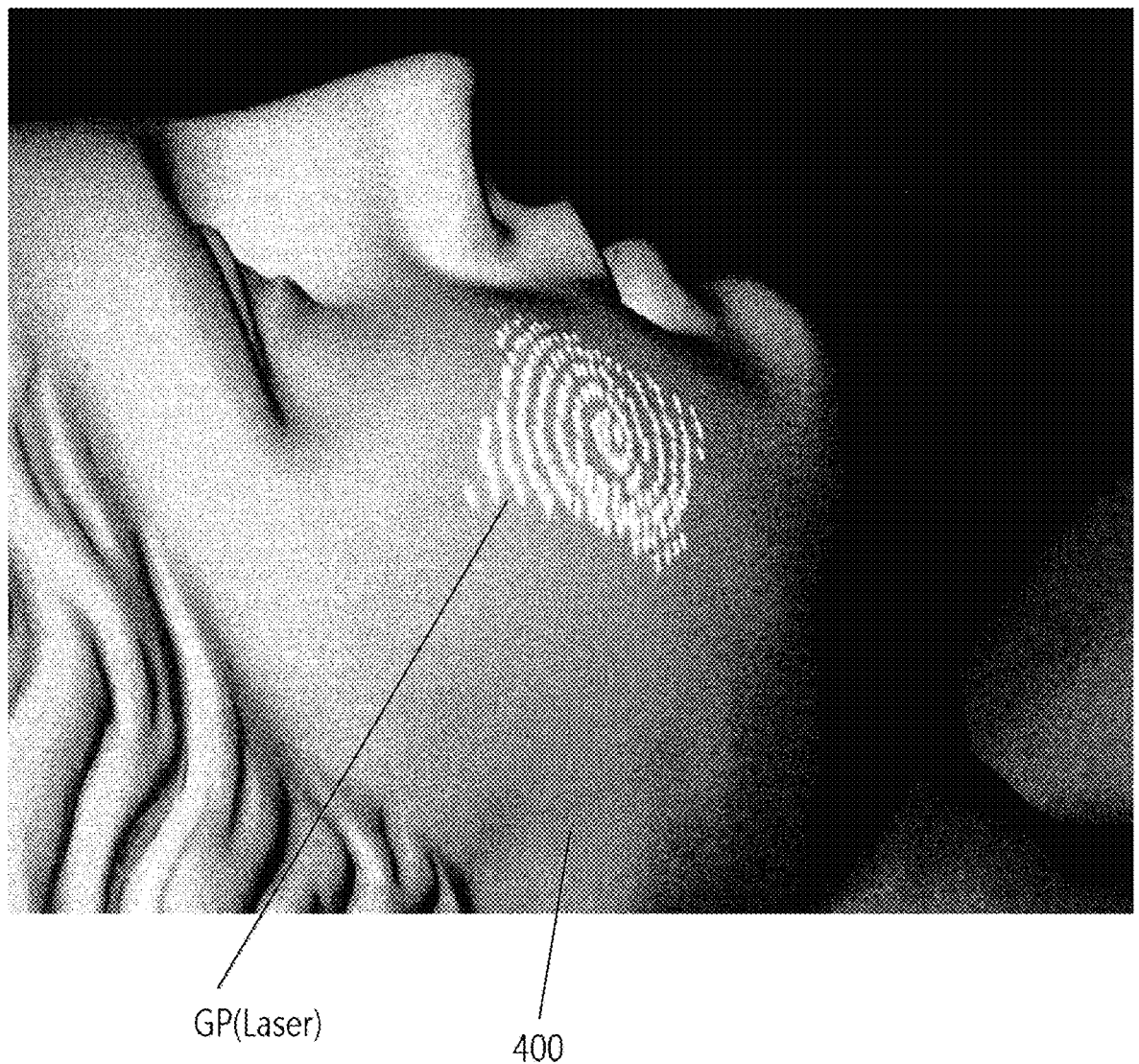

The laser irradiation experiment conducted by using the laser irradiation apparatus 10 according to the present invention is described in FIGS. 21 and 22.

Referring to FIG. 21, it is disclosed an example that the robot arm 100, including a laser emitter, a motor, a motor drive, a reflecting mirror and an end-effector (EE), irradiates the laser onto the surface of the object 400 that is the plaster cast of head shape.

The motors and the motor drive may operate the robot arm 100.

When the laser emitter is emitted the laser, the reflecting mirror may reflect at a predetermined angle thereby reaching the laser to the end-effector.

Then, the end-effector may irradiate the laser on the surface of the object 400.

Referring to FIG. 22, it may be confirmed that the guide path (GP) is set in the spiral on the surface of the object 400. FIG. 22 shows that it is photographed the laser irradiation on the surface of the object 400 in a constant duration and implemented by the shape of the guide path (GP).

On the other hand, it is possible to stop the laser irradiation depending on the conditions or to modify the guide path. The detailed explanation will be described as follows.

Figure 23:
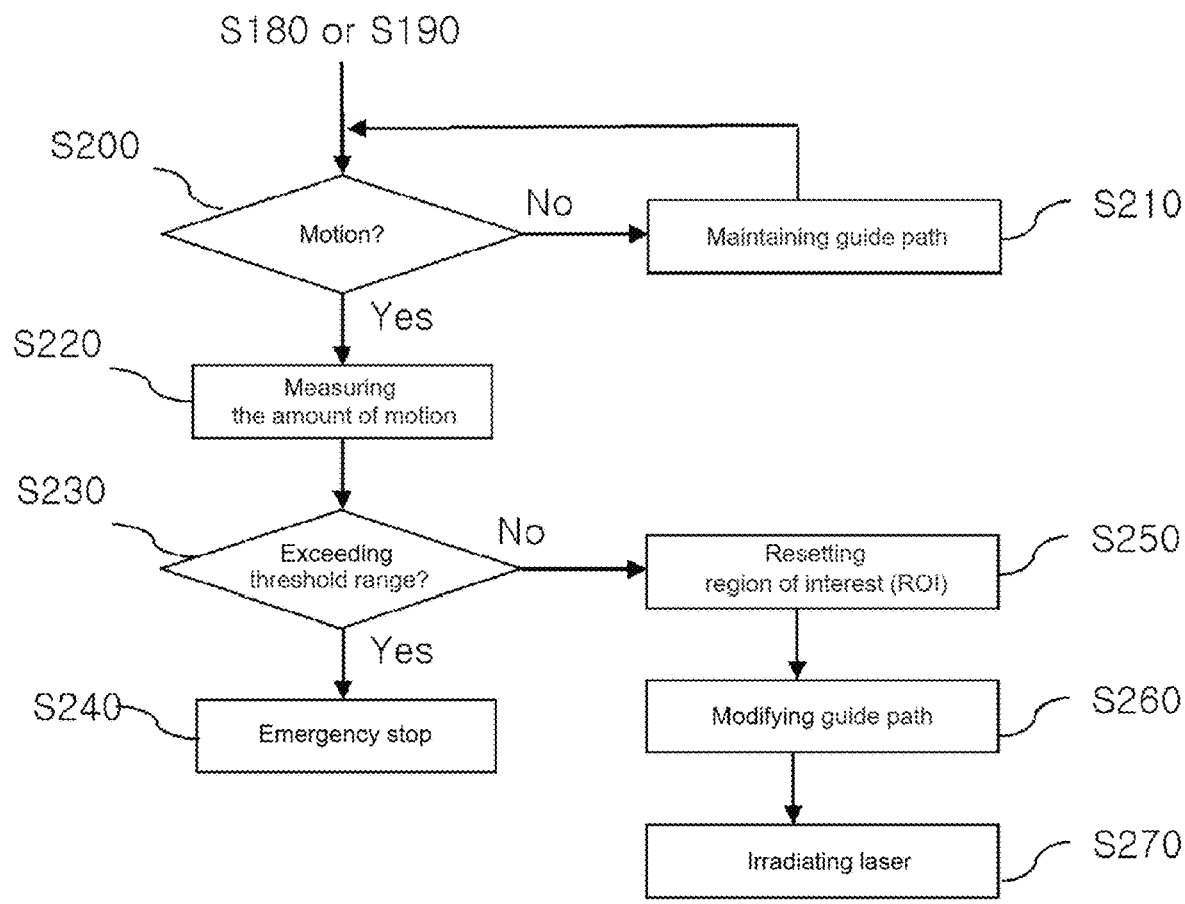

Referring to FIG. 23, the motion of the object 400 may be determined after setting the guide path (GP) or irradiating the laser (S200). For example, if the object 400 is a person's head, it may be determined whether there is a motion in a corresponding section or not by looking at a specific portion such as a nose, both eyes. Or, if the surface of the object 400 is moved, for example, the skin of a person is moved cause by the reasons such as convulsions in the skin of a person's face, it may be considered that the movement of the object 400 is exist.

As determined result, if there is no motion of the object 400, it may be maintained a predetermined guide path (GP) (S210).

On the other hand, if it is determined that the motion of the object 400 may be measured, it may measure the amount of motion of the object (400) (S220). The measurement of the amount of motion of the object 400 means to be determined that how long the object 400 is moved.

It is determined that whether the motion amount exceeds a threshold range previously set or not as the result of measuring the motion amount (S230).

It determined that, if the motion amount of the object 400 is greater than the threshold range previously set, it is possible to perform the emergency stop mode (S240). In this case, it is possible to urgently stop the laser irradiation.

On the other hand, if the motion amount of the object 400 does not exceed the threshold range, the region of interest (ROI) may be reset in consideration of the motion amount (S250).

In this embodiment, it is considered that the motion controlling unit 220 compensates or corrects the guide path, when the scanner 300 collects the motion of the object 400 and the vision controlling unit 210 newly reset the region of interest (ROI).

In addition, the guide path (GP) may also be modified corresponding to the reset of the region of interest (ROI) (S260).

Figure 24:
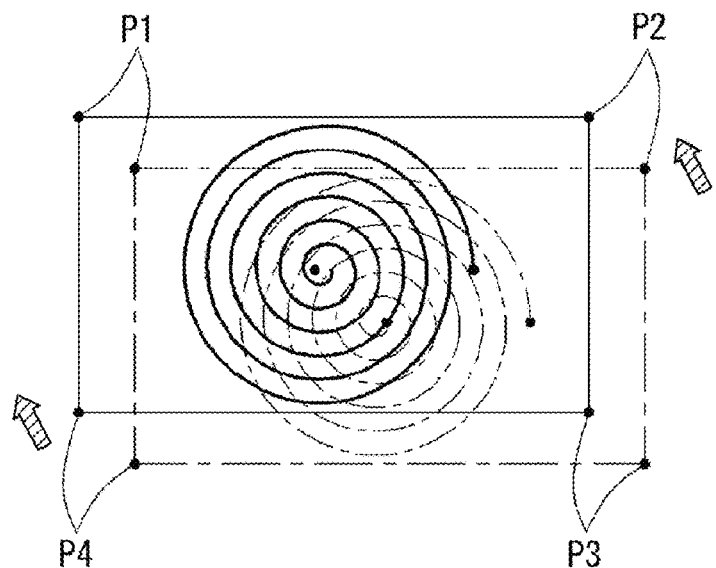

For example, as in the case of FIG. 24, if the object 400 is moved toward left upper side 1 cm, then the region of interest (ROI) is also moved toward the left upper side 1 cm. Correspondingly, the guide path (GP) may also be moved toward the upper left 1 cm.

Then, the laser may be irradiated on the surface of the object 400 corresponding to the modified guide path (GP) (S270).

As such, if the motion of the object 400 is occurred in the laser treatment process, it may be possible to modify the guide path (GP) in real time according to the motion of the object 400.

On the other hand, in the above description, it is described the embodiment as below that the object 400 is moved up, down, left or right on the same plane, it may be also be adapted when moving back and forth by maintaining the interval between the end-effector (EE) of the laser irradiation apparatus and the surface of the object 400.

In case that the vibration is generated and the force is applied in the laser irradiation apparatus 10, it is possible to perform the emergency stop mode.

Figure 25:
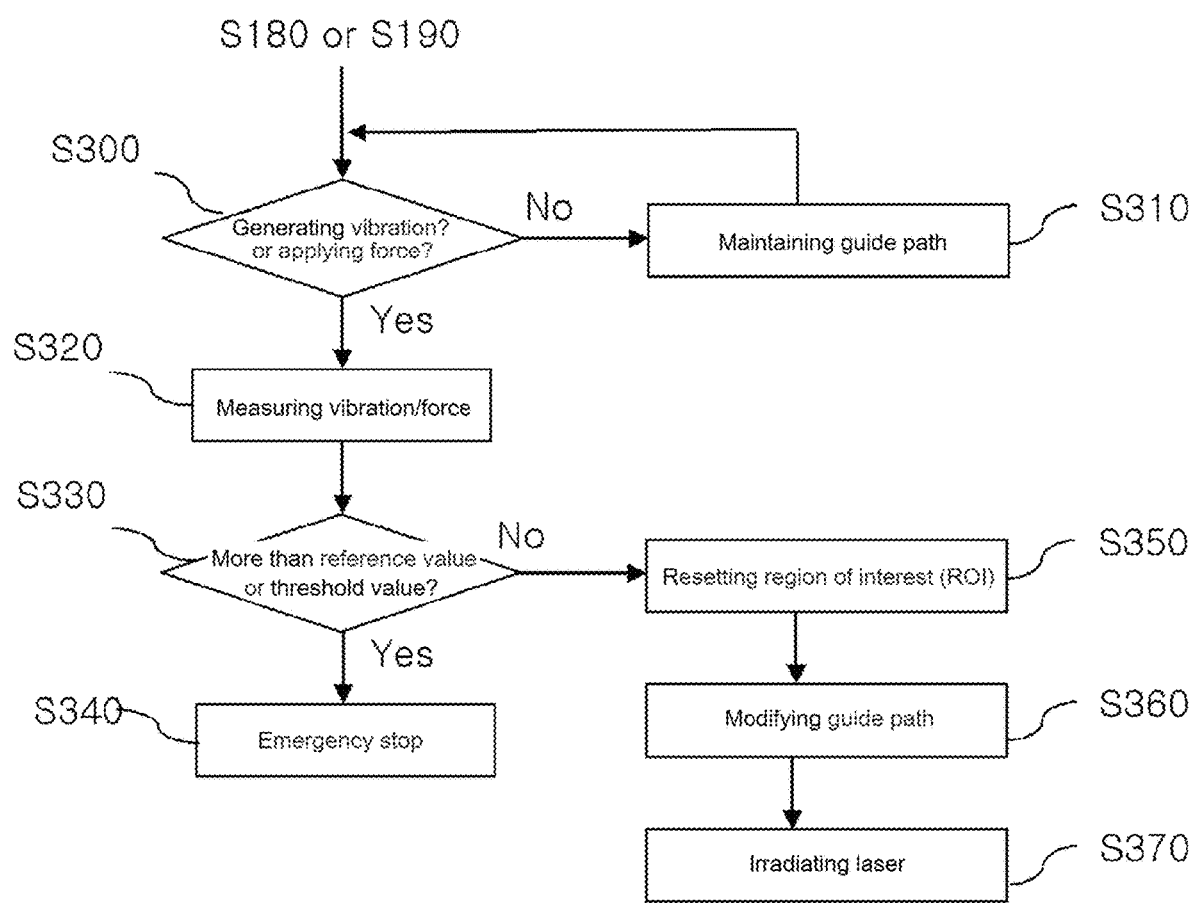

For example, as shown in FIG. 25, it may be determined that whether the vibration is generated or the force is applied or not after setting the guide path (GP) or irradiating the laser (S300).

As determined result, if the vibration is not generated or the force is not applied, it may be maintained the predetermined guide path (GP) (S310).

On the other hand, it is determined that the vibration is generated, or the force is applied, it may measure the vibration and/or the force (S320).

As the measured result, it may be determined that whether the vibration is generated more than a reference value previously set, or applied the force more than a threshold value previously set (S330).

As the measured result, if the vibration is generated more than the reference value, or applied the force more than the threshold value, it may perform the emergency stop mode (S340). In this case, it is possible to urgently stop the laser irradiation.

On the other hand, if the vibration is generated less than the reference value, or applied the force lower more than the threshold value, it may reset the region of interest (ROI) in consideration of the vibration and/or the force (S350).

In addition, the guide path (GP) may also be modified corresponding to the reset of the region of interest (ROI) (S360).

Then, the laser may be irradiated on the surface of the object 400 corresponding to the modified guide path (GP) (S370).

For example, the laser irradiation apparatus 10 may be urgently stopped to cease the laser irradiation where the vibration equal to or larger than the reference value is generated in the robot arm 100 when someone touches the laser irradiation apparatus or touches a table on which the patient is lying, or an earthquake occurrence in the course of the treatment procedure. Alternatively, the laser irradiation apparatus 10 may be urgently stopped to stop the laser irradiation, during the treatment procedure, the user (doctor or the like) finds a procedure error and holds the robot arm 100 by hand thereby applying the force equal to or greater than a threshold value to the robot arm 100.

For the robot arm to be applied to the laser irradiation apparatus, it will be described above referring to the accompanying drawings as follows.

FIGS. 26 to 34 are views for explaining the embodiment of the structure of the robot arm, it may be omitted the explanation as described above in the following description. The explanation described as above may be implemented using the robot arm 100.

The first link 130, the second link 140, the first end part 161, the second end part 162 and the third end part 163 may be used as a hollow type pope, respectively. Accordingly, the laser emitted from a laser unit 500 may be transferred to the end-effector 101 through the first link 130, the second link 140, the first end part 161, and the second end part 162, and the third end part 163 as reflecting to the predetermined mirror. More detailed explanation will be described as below.

Referring to FIGS. 26-30, the robot arm 100 may include the first base part 110, the second base part 120, the first link 130, the second link 140, an auxiliary link 150, a laser unit 500, the first motor part 170, the second motor part 180 and the third motor part 190.

The laser unit 500 is disposed on the first base part 110 to generate the laser.

The second base part 120 may be coupled to be rotatable onto the first base part 110.

Figure 28:
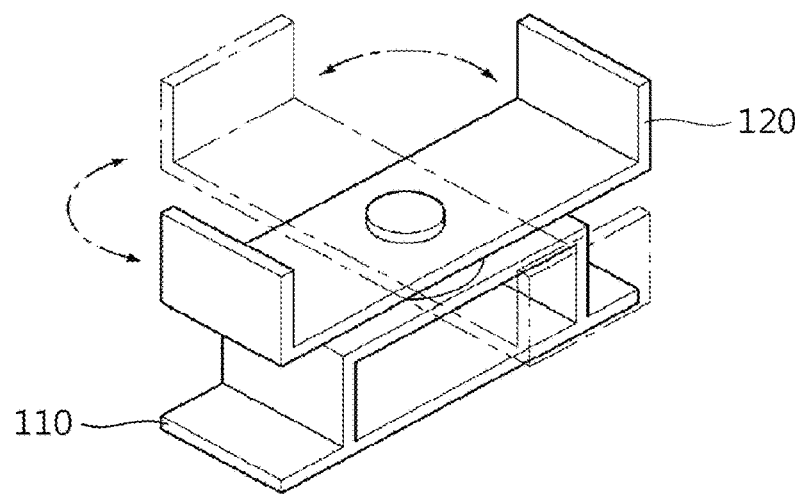

The second base part 120, as shown in FIG. 28 may confirm that of swinging onto the first base part 110.

The first motor part 170 is disposed on the first base part 110 to rotate the second base part 120.

Figure 26:
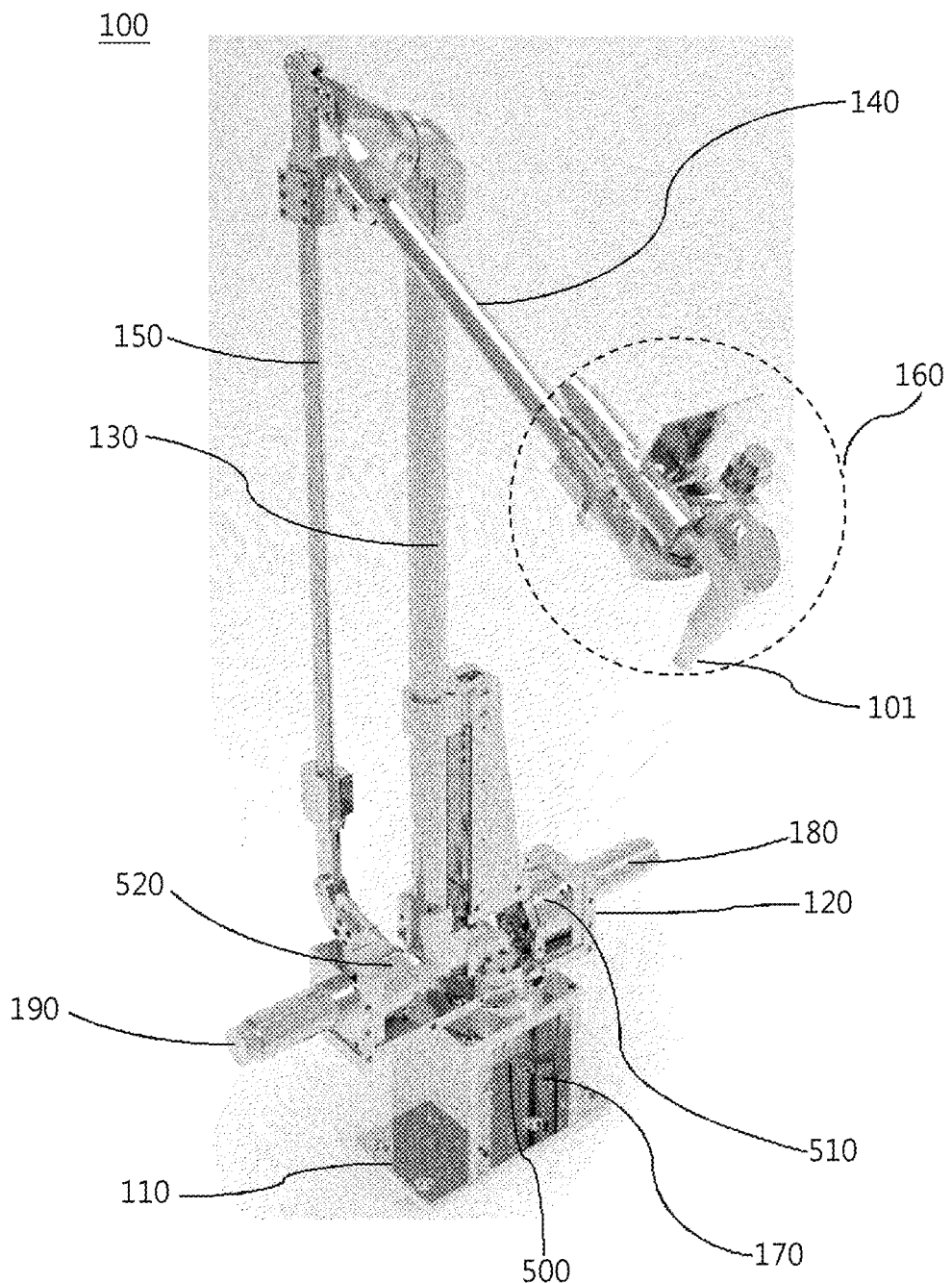
FIGS. 26 to 34 are views for explaining embodiments of a structure of a robot arm according to the present invention.
Figure 27:
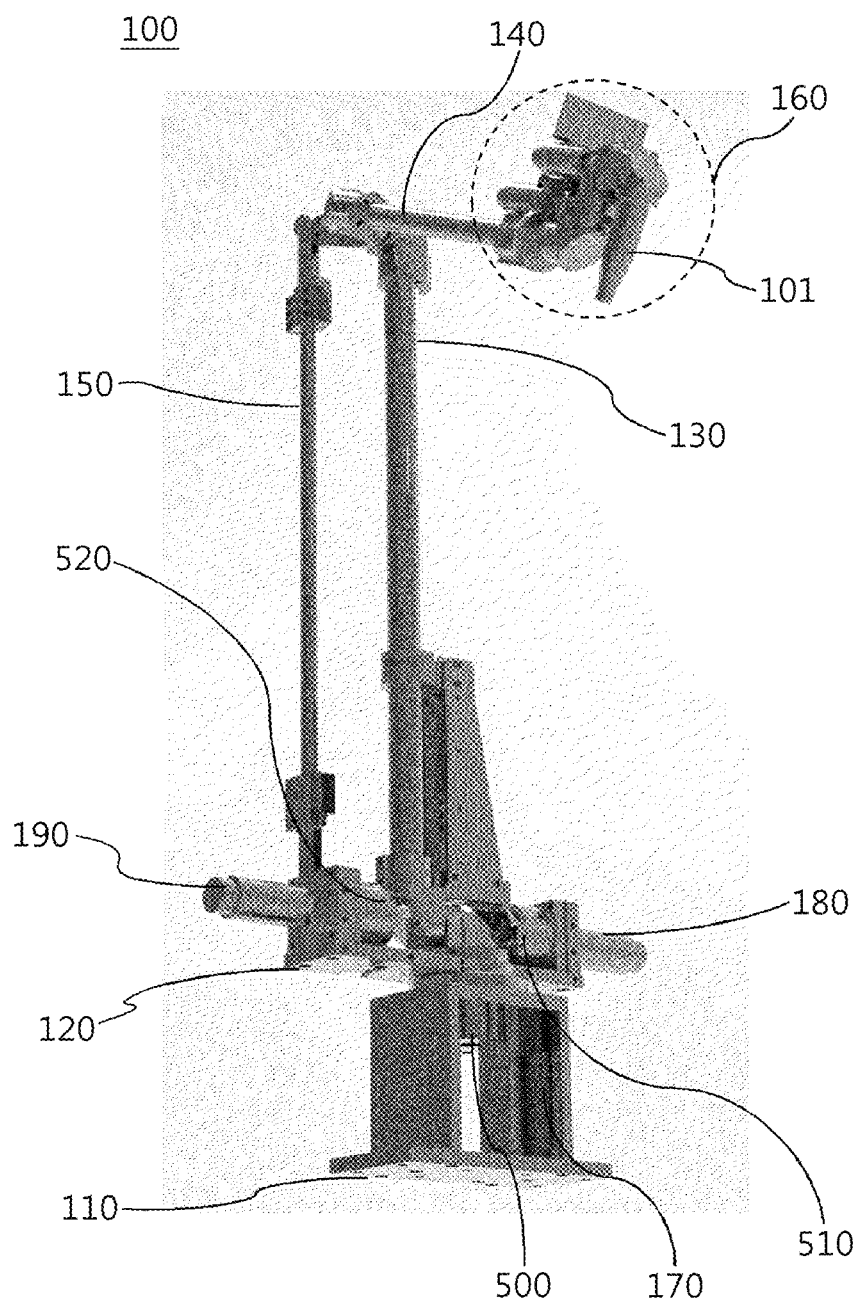
Figure 29:
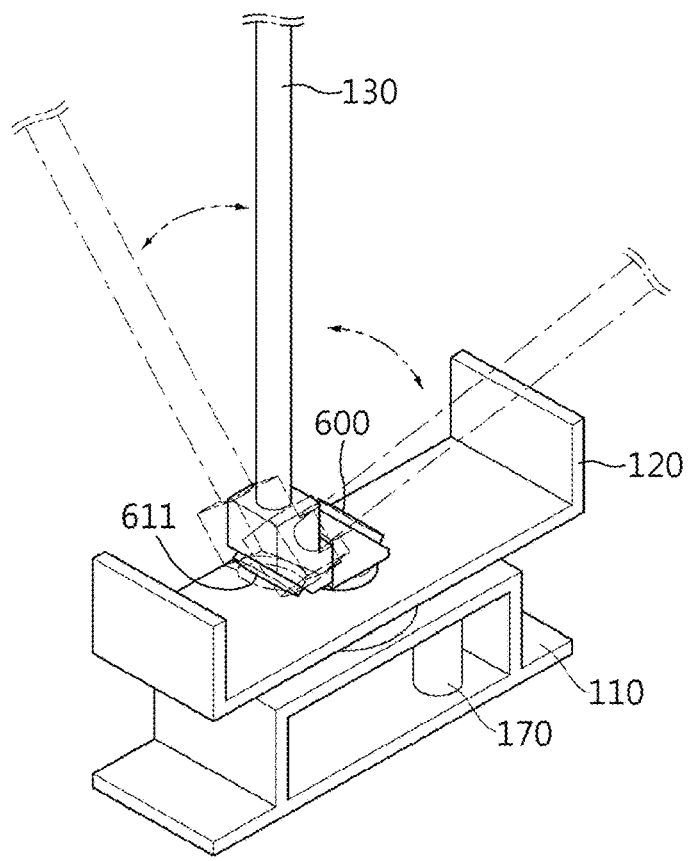

Referring to FIGS. 26, 27 and 29, the first link 130 may be coupled to enable swing onto the second base part 120.

The second motor part 180 is disposed on the second base part 180 to swing the first link 130.

FIG. 29 shows an example of a case that the first link 130 is swinging about the connecting portion with the second base part 120.

The first mirror part 600 may be disposed in the second base part 120. The first mirror part 600 is capable of reflecting the laser emitting from to the laser unit 500 towards the first link 130 corresponding to the laser unit 500.

The second mirror part 610 corresponding to the first mirror part 600 may be disposed in the first link 130. The second mirror part 610 may include the first sub-mirror 611 and the second sub-mirror 612 as disclosed in FIGS. 29 and 30.

The first sub-mirror 611 may correspond to the first mirror part 600, while the second sub-mirror 612 may correspond to the first sub-mirror 611.

The second mirror part 610 may reflect the laser, reflected by the first mirror part 600, toward the second link 140. Specifically, the first sub-mirror 611 of the first mirror part 610 reflects the laser reflected by the first mirror part 600 toward the second sub-mirror 612, the second sub-mirror 612 may reflect the laser reflected by the first mirror part toward the third mirror part 620 disposed in the second link 140. The third mirror part 620 may reflect the laser reflected by the second sub-mirror 612 toward an end part 160.

Figure 30:
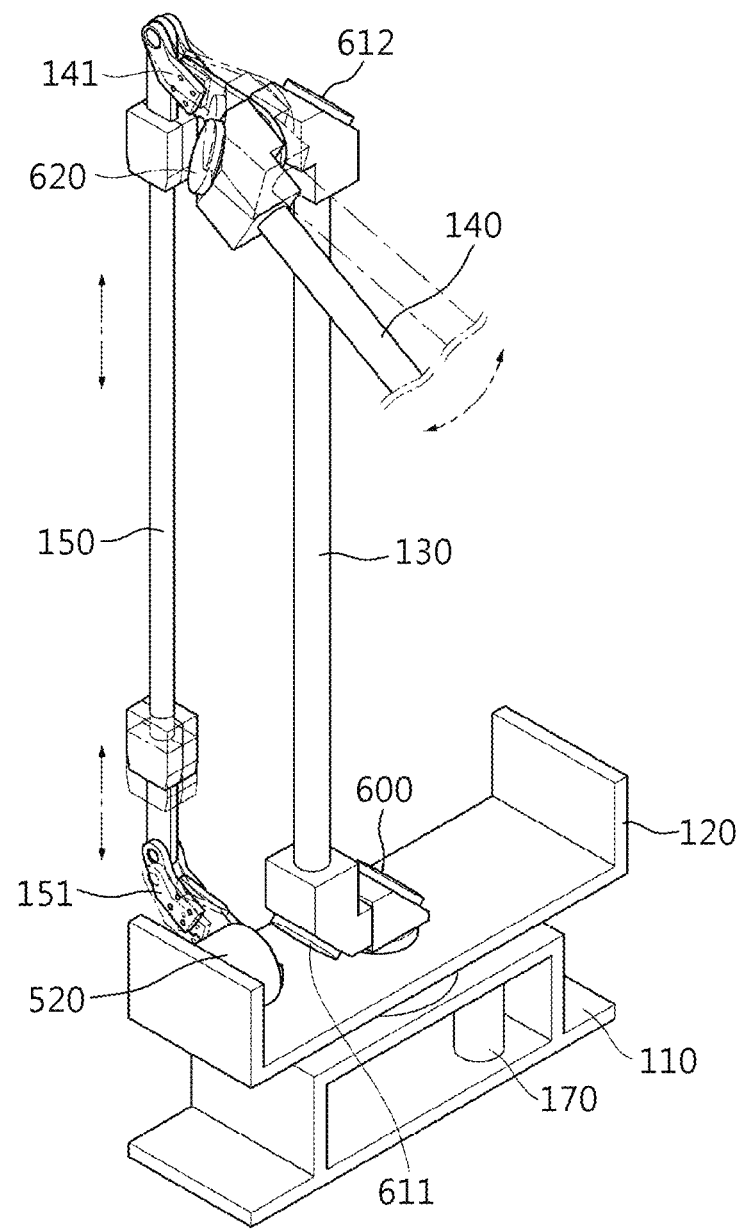

Referring to FIGS. 26, 27 and 30, the second link 140 may be coupled to enable to swing onto the first link 130.

One end of the auxiliary link 150 is coupled to the second base part 120, the other end may be coupled to the second link 140. To this end, it is arranged the first extending arm 141 extending in the extension direction that is the opposite direction of the second link 140 in the end of the second link 120. In addition, the second reduction gear 520 is arranged in the second base part 120, and a second extending arm 151 may be arranged in the second reduction gear 520.

One end of the auxiliary link 150 is coupled to the second base part 120 by connecting to the second extending arm 151, while the other end of the auxiliary link 150 is coupled to the second link 140 by connecting to the first extending arm 141.

The third motor part 190 is arranged on the second base part 120, and may swing the second link 140 through the secondary link 150. Specifically, the third motor part 190 may swing the secondary link 150 up and down directions, thereby swing the second link 140 may swing by the up and down movement of the auxiliary link 150. For example, the third motor part 190 is rotated, the second extending arm 151 is moving, also the auxiliary link 150 is moving up and down directions, thus, the second link 140 may swing as shown in FIG. 30.

The second reduction gear 520 is coupled to the third motor part 190, the number of rotations of the third motor part 190 may be reduced to the required number of rotations. In some cases, the second reduction gear 520 may be omitted.

As shown in FIGS. 26 and 27, the first reduction gear 510 may be arranged in the second base part 120.

The first speed reducer 510 is connect to the second motor part 180, the number of rotations of the second motor part 180 may be reduced to the required the number of rotations. In some cases, the first reduction gear 510 may be omitted.

The end part 160 may be coupled to the second link 140.

Figure 31:
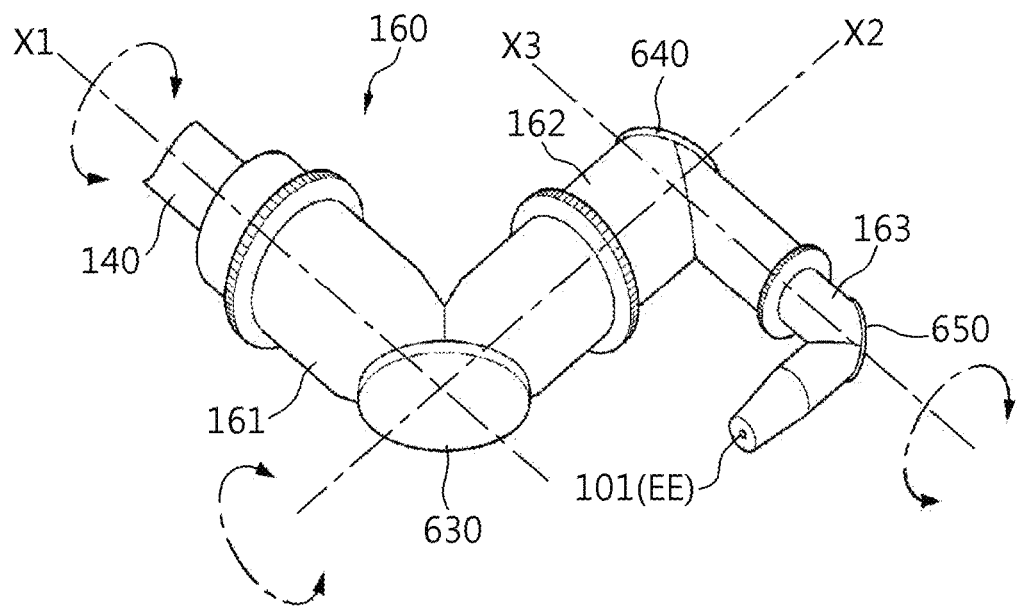
Figure 32:
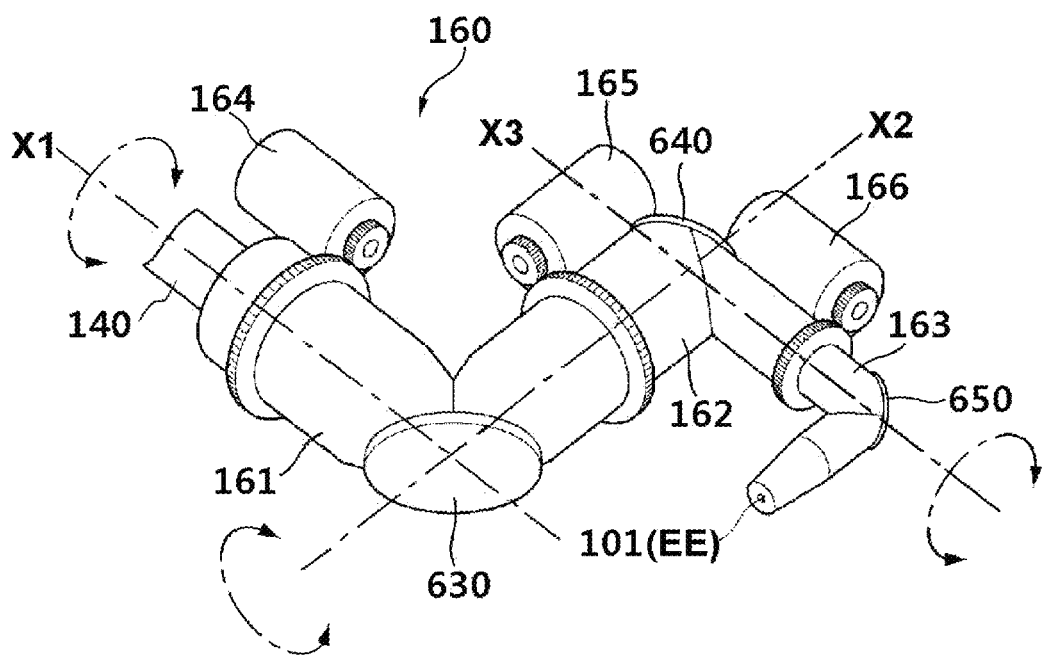

Referring to FIGS. 31 and 32, the end part 160 has the first end part 161, the second end part 162 and the third end part 163.

In addition, the end part 160 may include the end-effector (EE) 101 for irradiating the laser to the object, for example, the skin of the patient. The end-effector 101 may be arranged on the third end part 163.

The first end part 161 is couple to the second link 140 and may rotate onto the first axis X1.

The second end part 162 may couple to the end part 161, and may be rotated onto the second axis X2 perpendicular to the first axis X1.

The third end part 163 is coupled to the second end part 162 and rotatable onto the third axis X3 perpendicular to the second axis X2.

The first, second, and third end parts 161, 162, and 163 may be each "]" elbow shaped pipe.

The fourth mirror part 630 corresponding to the third mirror part 620 may be arranged in the first end part 161. For example, the fourth mirror part 630 may be arranged in the bent portion of the first end part 161.

In addition, the fifth mirror part 640 corresponding to the fourth mirror part 630 may be arranged in the second end part 162. For example, the fifth mirror part 640 may be arranged in the bent portion of the second end part 162.

The sixth mirror part 650 corresponding to the fifth mirror part 640 may be arranged in the third end part 163. For example, the sixth mirror part 650 may be arranged in the bent portion of the third end part 163.

The first end part 161 is rotatable onto the first axis X1 by the fourth motor part 164. The fourth motor part 164 may be arranged on the first end part 161.

The second end part 162 may be rotated onto the second axis X2 by the fifth motor part 165. The fifth motor part 165 may be arranged in the second end part 162.

The third end part 163 may be rotated onto the third axis X3 by the sixth motor part 166. The sixth motor part 166 may be arranged on the third end part 163.

Figure 33:
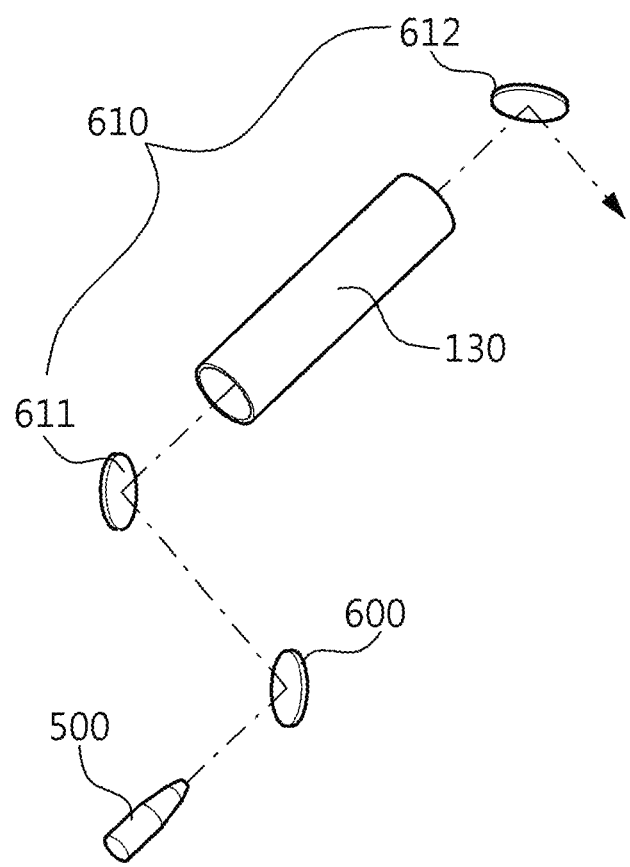
Figure 34:
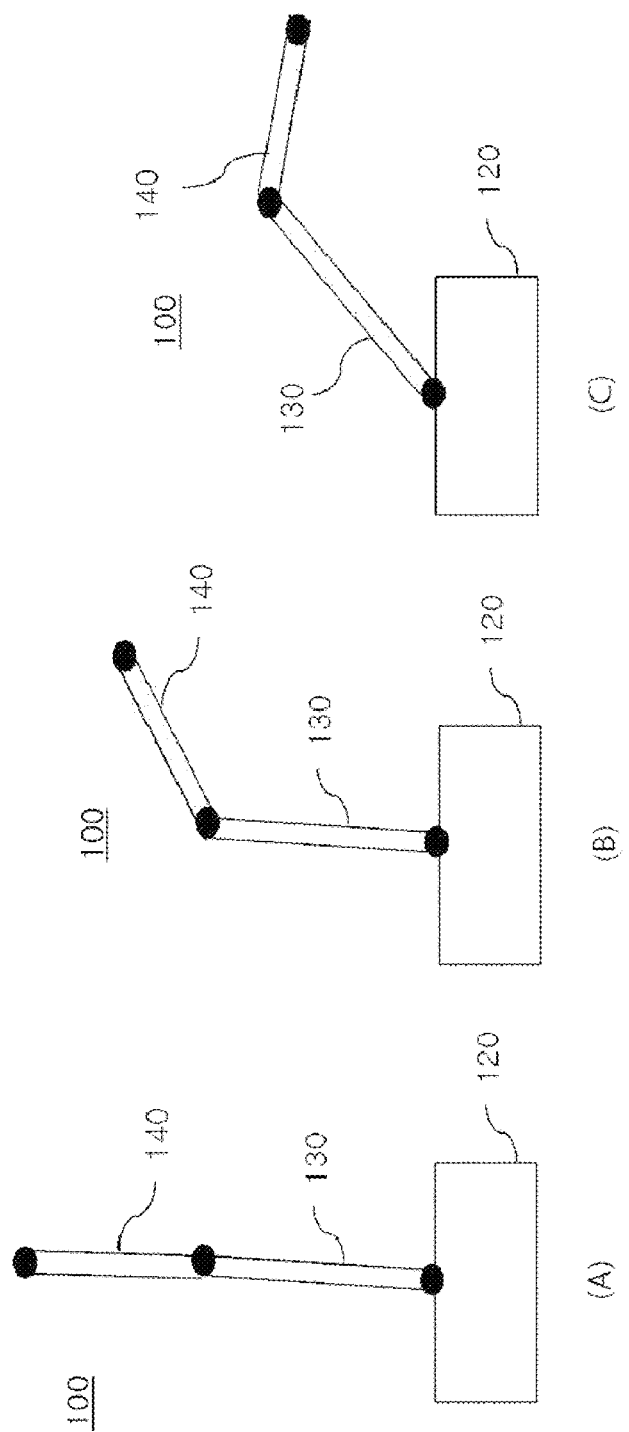

If the laser unit 500 irradiates the laser, as shown in FIG. 33, the laser may be directed to the third mirror 620 by reflecting the first mirror part 600, and the first sub-mirror 611 and the second sub-mirror mirror 612 of the second mirror part 610.

Then, the laser reflected by the second sub-mirror 612 may be reached to the end-effector 101 through the third mirror part 620, the fourth mirror part 630, the fifth mirror part 640 and the sixth mirror part 650. The laser reached in the end-effector 101 may irradiate the laser to the outside.

On the other hand, the movement of the third end part 163 may be limited compared to the movement of the first end part 161 and/or the second end part 162.

For example, if the portion for irradiating the laser is determined, it maximally approaches the end-effector 101 to corresponding place by primarily moving the first link 130 and/or the second link 140. And it may be closer to the end-effector 101 in its place by moving the first end part 161 and/or the second end part 162. If it is difficult to approach the end-effector to a desired place with the movement of the first link 130, the second link 140, the first end part 161 and/or the second end part 162, then it may operate the end-effector by moving the third end part 163.

Or, third, it is possible to set to be minimized the maximum operational range of the end part 163 than the operational range of the first end part 161 and/or the second end part 162.

On the other hand, if the second mirror part may be configured with the first sub-mirror 611 and the second sub-mirror 612, the operational radius of the robot arm 100 may be widen, thereby improving the efficiency of the laser treatment.

Specifically, as shown in FIG. 30, when the first sub-mirror 611 is arranged on an end of the first link 130, and second sub-mirror 612 is also arranged on the other end of the first link 130, the laser irradiated from the laser unit 500 may be effectively reflected toward the second link 140 and may be set more freely the swinging direction of the second link 140. For example, it is possible to equally make of the swing directions of the first link 130 and the second link 140.

In this case, as shown in FIGS. 34(A), 34(B), and 34(C), the operational radius of the robot arm 100 may be widened, since the first link 130 and the second link 140 may move in the same direction.

Although the configuration of the robot arm 100 according to the embodiment of the present invention has been described above with reference to FIGS. 26 to 34, the present invention is not limited to the illustrated configuration, some of the illustrated components may be omitted or additional components may be added as needed.

For example, the first link 130 coupled to be swing on the second base unit 120 may be omitted, if necessary.

Although the embodiment of the present invention has been described with reference to the laser irradiation apparatus using the robot arm, but the present invention is not limited thereto. In addition, it may be applicable to control movement patterns in various types of a gantry type laser irradiation apparatus for wrapping a patient's face or the laser irradiating apparatus in the shape of the laser array patch attached to a patient's face.

Further, although the present invention is described as the example with reference to the laser irradiation apparatus using the robot arm, the technical construction of the present invention may be applicable to a variety of energy based medical device, for treating the skin, using the high frequency, ultrasound, IPL (Intense Pulse Light), Psoralen-UV-A (PUVA), etc.

On the other hand, the embodiment of the present invention is described in referring to an example that the robotic arm 100 of the laser irradiation apparatus delivers the laser to the end-effector (EE) from the laser emitter using the plurality of reflecting mirrors, but the present invention is not limited to thereto, but the laser may be delivered to the end-effector (EE) by the optical fiber.

The laser irradiation method using the robot arm according to the present invention may be stored in a computer-readable recording medium manufactured as a program to be executed in a computer, examples of the computer-readable recording medium include ROM, RAM, CD-ROM, a magnetic tape, a floppy disc, optical data storage devices, and it is implemented in the form of carrier waves (such as data transmission through the Internet).

Further, the computer-readable recording medium is distributed over network coupled computer systems so that the computer readable code is stored and executed in a distributed fashion. Then, the functional (functional) programs, codes, and code segments for accomplishing the present invention can be easily construed by programmers skilled in the art to which the invention pertains.

In this way, the above-described technical construction of the present invention it will be appreciated that without the person skilled in the art changing the technical spirit or essential features of the invention may be embodied in other specific forms.

Therefore, the embodiment described in the above examples should be understood as not be illustrative and not restrictive in all respects, and becomes the scope of the invention is indicated by the claims below rather than the foregoing description, the meaning and scope of the claims and all such modifications as derived from the equivalent concept be construed as being included in the scope of the invention.

What is claimed is:

1. A laser irradiation apparatus using a robot comprising:
a scanner for scanning an object to collect a raw data;
a vision controlling unit for constituting a three-dimensional image of the object based on the raw data, and setting a region of interest (ROI) on a surface of the object in the three-dimensional image;
a motion controlling unit for setting a spiral guide path passing through the region of interest; and
a robot arm, having an end-effector, for irradiating a laser on the surface of the object corresponding to the spiral guide path,
wherein the robot arm comprises:
a first base part;
a second base part rotatably coupled to the first base part;
a first link being rotatably coupled to the second base part;
a second link rotatably coupled to the first link;
an auxiliary link having one end thereof coupled to the second base part and the other end thereof coupled to the second link;
a laser unit, disposed on the first base part, for generating the laser;
a first motor part, disposed on the first base part, for rotating the second base part;
a second motor part, disposed on the second base part, for rotating the first link; and
a third motor part, disposed on the second base part, for rotating the second link through the auxiliary link,
wherein when a motion of the object is generated during irradiation process of the laser, the motion controlling unit stops the irradiation process if the motion of object exceeds a preset threshold range, and wherein when the motion of the object does not exceed the preset threshold range, the motion controlling unit modifies the region of interest (ROI) and the spiral guide path based on the motion of the object.

2. The laser irradiation apparatus according to claim 1, wherein the vision controlling unit detects a region of therapy where at least one of a color or a contrast is different from surroundings on the surface of the object, and sets the region of interest to include the region of therapy.

3. The laser irradiation apparatus according to claim 2, wherein the spiral guide path passes through the region of therapy, and the robot arm irradiates the laser on the region of therapy.

4. The laser irradiation apparatus according to claim 2, wherein the motion controlling unit adjusts a least one of a frequency, an irradiation time, a number of irradiations, and a fluence of the laser according to at least one of a degree of a color or a brightness of the region of therapy.

5. The laser irradiation apparatus according to claim 1, wherein the scanner comprises:
a color sensor for photographing a two-dimensional color image; and
an IR projector and an IR sensor for obtaining a third depth data.

6. The laser irradiation apparatus according to claim 1, wherein the motion controlling unit stops the irradiation process of the laser when a vibration for the object occurs which is greater than a preset reference value.

7. The laser irradiation apparatus according to claim 1, wherein the motion controlling unit stops the irradiation process of the laser when a force is applied to the robot arm which is greater than a preset threshold value.

8. The laser irradiation apparatus according to claim 1, wherein the third motor part moves the auxiliary link in up and down directions, and the second link is rotated by the up and down motion of the auxiliary link.

* * * * *